US012036180B2

(12) United States Patent
Berdahl et al.

(10) Patent No.: US 12,036,180 B2
(45) Date of Patent: Jul. 16, 2024

(54) EYE TREATMENT APPARATUS AND METHOD WITH INDEPENDENT PRESSURE SOURCES

(71) Applicant: BALANCE OPHTHALMICS, INC., Sioux Falls, SD (US)

(72) Inventors: John Berdahl, Sioux Falls, SD (US); George Tsai, Mission Viejo, CA (US)

(73) Assignee: Balance Ophthalmics, Inc., Sioux Falls, SD (US)

( * ) Notice: Subject to any disclaimer, the term of this patent is extended or adjusted under 35 U.S.C. 154(b) by 582 days.

(21) Appl. No.: 17/130,094

(22) Filed: Dec. 22, 2020

(65) Prior Publication Data
US 2021/0106492 A1 Apr. 15, 2021

Related U.S. Application Data

(63) Continuation of application No. PCT/US2019/039399, filed on Jun. 27, 2019.
(Continued)

(51) Int. Cl.
A61H 5/00 (2006.01)
A61B 3/16 (2006.01)
(Continued)

(52) U.S. Cl.
CPC .............. *A61H 5/00* (2013.01); *A61H 9/00* (2013.01); *A61B 3/16* (2013.01); *A61B 5/031* (2013.01);
(Continued)

(58) Field of Classification Search
CPC .. A61H 5/00; A61H 5/005; A61H 9/00; A61F 9/00781; A61F 2013/0028
See application file for complete search history.

(56) References Cited

U.S. PATENT DOCUMENTS 4,387,707 A * 6/1983 Polikoff ................ A61F 9/007
601/37
5,625,426 A * 4/1997 Liu ........................ A61H 9/005
351/158
(Continued)

FOREIGN PATENT DOCUMENTS

JP 2010504768 2/2010
JP 7410362 12/2023
(Continued)

OTHER PUBLICATIONS

"International Application Serial No. PCT/US2019/039399, International Search Report dated Oct. 8, 2019", 7 pgs.
(Continued)

Primary Examiner — Joseph D. Boecker
Assistant Examiner — Thomas W Greig
(74) Attorney, Agent, or Firm — Schwegman, Lundberg & Woessner, P.A.

(57) ABSTRACT

An apparatus can include a left cover, sized and shaped to fit over a left eye of a patient to define a left cavity between the left cover and an anterior surface of the left eye and a right cover, sized and shaped to fit over a right eye of the patient to define a right cavity between the right cover and an anterior surface of the right eye. The apparatus can include a left pressure source to apply a left working fluid to the left cavity, the left pressure source capable of generating a left cavity pressure including a left negative gauge pressure and a right pressure source to apply a right working fluid to the right cavity, the right pressure source capable of generating a right cavity pressure including a right negative gauge pressure, where the right pressure source can be separate from the left pressure source. The left pressure source can be configured to generate a left cavity pressure independently of the right pressure source and the right pressure source can
(Continued)

be configured to generate a right cavity pressure independently of the left pressure source.

20 Claims, 12 Drawing Sheets

Related U.S. Application Data

(60) Provisional application No. 62/691,210, filed on Jun. 28, 2018.

(51) Int. Cl.
*A61B 5/03* (2006.01)
*A61H 9/00* (2006.01)

(52) U.S. Cl.
CPC ............. *A61H 2201/018* (2013.01); *A61H 2201/1409* (2013.01); *A61H 2201/1604* (2013.01); *A61H 2201/165* (2013.01); *A61H 2201/5002* (2013.01); *A61H 2230/00* (2013.01)

(56) References Cited

U.S. PATENT DOCUMENTS

| | | | |
|---|---|---|---|
| 5,927,281 A | 7/1999 | Monteleone et al. | |
| 2004/0237969 A1* | 12/2004 | Fuller | A61H 35/02 128/858 |
| 2013/0035651 A1* | 2/2013 | Tout | A61M 1/00 604/319 |
| 2013/0238015 A1* | 9/2013 | Berdahl | A61B 5/6803 606/204.25 |
| 2014/0275935 A1* | 9/2014 | Walsh | A61B 3/0083 600/398 |
| 2015/0313761 A1* | 11/2015 | Berdahl | A61B 5/6803 606/204.25 |
| 2018/0042805 A1* | 2/2018 | Lin | A61H 9/0057 |
| 2020/0030150 A1* | 1/2020 | Oduncu | A61F 9/00781 |

FOREIGN PATENT DOCUMENTS

| | | | | |
|---|---|---|---|---|
| JP | 2023184682 | | 12/2023 | |
| WO | WO-2007136993 | A1 | 11/2007 | |
| WO | 2017035406 | | 3/2017 | |
| WO | WO-2017156050 | A1 | 9/2017 | |
| WO | WO-2018106839 | A2 * | 6/2018 | ............. A61F 11/00 |
| WO | WO-2018174835 | A1 | 9/2018 | |
| WO | WO-10154926 | | 12/2018 | |
| WO | WO-2020006169 | A1 | 1/2020 | |

OTHER PUBLICATIONS

"International Application Serial No. PCT/US2019/039399, Written Opinion dated Oct. 8, 2019", 7 pgs.

Suzuki Jr, Emilio Rintaro, et al., "Dynamic contour tonometry in asymmetricglaucoma patients", Clinical Ophthalmology, (Apr. 10, 2012), 555-559.

"European Application Serial No. 19740219.1, Communication Pursuant to Article 94(3) EPC dated Feb. 22, 2023", 4 pgs.

"Japanese Application Serial No. 2020-572543, Office Action dated Apr. 11, 2023", w English Translation, 6 pgs.

"European Application Serial No. 19740219.1, Response filed Jun. 5, 23 to Communication Pursuant to Article 94(3) EPC dated Feb. 22, 2023", 53 pgs.

"Japanese Application Serial No. 2020-572543, Response filed Jun. 28, 2023 to Office Action dated Apr. 11, 2023", w English claims, 12 pgs.

"Australian Application Serial No. 2019295731, First Examination Report mailed Mar. 25, 2024", 6 pgs.

"Chinese Application Serial No. 201980052543.9, Office Action mailed Dec. 6, 2023", W English Translation, 20 pgs.

\* cited by examiner

COEXTRUDED OR BONDED TUBING

COEXTRUDED COAXIAL TUBING

TUBE WITHIN A TUBE

EYE TREATMENT APPARATUS AND METHOD WITH INDEPENDENT PRESSURE SOURCES

CLAIM OF PRIORITY

This patent application is a continuation of International Application No. PCT/US2019/039399, entitled "Eye Treatment Apparatus and Method with Independent Pressure Sources", filed on Jun. 27, 2019, which claims the benefit of priority of U.S. Provisional Patent Application Ser. No. 62/691,210 to John Berdahl entitled "Eye Treatment Apparatus and Method with Independent Pressure Sources," filed on Jun. 28, 2018 which is hereby incorporated by reference in entirety.

BACKGROUND

A bilateral eye condition, such as a bilateral eye condition associated with glaucoma or optic disk edema, can silently steal the eyesight of a patient in the absence of proper care. The measurement of asymmetric intraocular pressure (IOP) levels in the patient, such as where different IOP levels can be sensed in the left eye and right eye of the patient, can indicate the presence of an eye condition and the need for different treatment regimens, such as a different treatment regimen for each of the left eye and right eye of the patient. As the progression of a bilateral eye condition can affect the left eye and the right eye of the patient at different rates, an apparatus that can apply separate treatment protocols, such as different treatment protocols for each of the left eye and the right eye, can greatly improve patient outcomes.

Dupps U.S. Pat. No. 7,935,058 mentions a system for characterizing biomechanical properties of tissue with an imaging system and a perturbation element that includes a transparent chamber and a pump.

Kang U.S. Pat. No. 5,807,357 mentions a compact nebulizer for treating the eyes including a goggles unit having an air hole and at least one air chamber communicating with the air hole and fitting over the user's eyes. A plurality of exhausting holes is made at the goggle unit for exhaust air.

Skiba U.S. Patent Application No. 2002/0124843 mentions a mask worn around the eyes with one or more fog outlets and an atomizer to nebulize medicine into a fog such that the fog discharges from the fog outlets to deliver medicine to one or more eyes.

Guillon U.S. Patent Application No. 2007/0265505 mentions an eye cover adapted to provide an enclosed area about the eyes of the user, a means for retaining the eye cover in position, and means for supplying dry air to the eye cover.

OVERVIEW

Eye conditions, such as glaucoma and optic disc edema, are estimated to affect more than 60 million people worldwide (ages 40-80) with prevalence growing to more than 110 million by 2040. While eye conditions are often bilateral (e.g., affecting both eyes of a patient), glaucoma and optic disk edema often do not affect both eyes equally or at the same progression rate. In practice, treatment of the eye condition with two different treatment regimens, such as a left treatment regimen for a left eye and a right treatment regimen for a right eye, can allow a care giver to customize a therapeutic treatment to a patient-specific condition, such as to greatly improve patient outcomes.

The present inventors have recognized, among other things, that there is a need in the art for systems and methods that can apply a treatment regimen to an eye, such as to apply a left treatment regimen to a left eye, a right treatment regimen to a right eye, or to simultaneously apply a left treatment regimen to the left eye and a right treatment regimen to the right eye, to treat, inhibit, or prevent an eye condition. The apparatus and methods described herein can control, such as establish, adjust, and maintain, an eye environment over a patient eye, such as at least one of a left eye environment over the left patient eye or a right eye environment over the right patient eye. In an example, control of the left eye environment can be independent of the right eye environment and control of the right eye environment can be independent of the left eye environment. In an example, an eye environment can include a working fluid where the working fluid can include a working fluid characteristic, such as at least one of a working fluid pressure or a working fluid composition.

Independent control of the left and right eye environments, such as applied to the patient left and right eyes respectively, can result in a treatment regimen tailored to the eye condition of each individual patient, such as to improve disease management that can enhance patient outcomes. This document describes, among other things, apparatus and methods for control, such as simultaneous, independent control, of a left eye environment over a left eye of a patient and a right eye environment over a right eye of a patient to treat, inhibit, or prevent an eye condition.

An apparatus can include a left cover, sized and shaped to fit over a left eye of a patient to define a left cavity between the left cover and an anterior surface of the left eye, and a right cover, sized and shaped to fit over a right eye of the patient to define a right cavity between the right cover and an anterior surface of the right eye. The apparatus can include a left pressure source to apply a left working fluid to the left cavity, such as a left pressure source configured to adjust fluid pressure in the left cavity. The left pressure source can generate a left cavity pressure such as a left cavity gauge pressure including a positive left cavity gauge pressure and a negative left cavity gauge pressure. The apparatus can include a right pressure source to apply a right working fluid to the right cavity, such as a right pressure source configured to adjust fluid pressure in the right cavity. The right pressure source can generate a right cavity pressure, such as a right cavity gauge pressure including a positive right cavity gauge pressure and a negative right cavity gauge pressure. The right pressure source can be separate from the left pressure source, such as the left pressure source can be configured to generate a left cavity pressure independently of the right pressure source and the right pressure source can be configured to generate a right cavity pressure independently of the left pressure source. In generating left cavity pressure in the left cavity with the left pressure source and right cavity pressure in the right cavity with the right pressure source, the apparatus can apply different gauge pressure to each of the left and right eye independently, such as to improve treatment of an eye condition by tailoring a therapeutic pressure regimen to each of the left eye and the right eye.

An overview of certain non-limiting aspects of the present subject matter is provided below.

Aspect 1 can include or use subject matter (such as an apparatus, a system, a device, a method, a means for performing acts, or a device readable medium including instructions that, when performed by the device, can cause the device to perform acts), such as an apparatus to apply a treatment regimen to an eye, such as to apply a left treatment regimen to a left eye, a right treatment regimen to a right eye, or to simultaneously apply a left treatment regimen to the left eye and a right treatment regimen to the right eye, to treat, inhibit, or prevent an eye condition. A left cover, sized and shaped to fit over a left eye of a patient can define a left cavity between the left cover and an anterior surface of the left eye. A left pressure source, in communication with the left cavity, can be configured to adjust fluid pressure in the left cavity. A right cover, sized and shaped to fit over a right eye of the patient can define a right cavity between the right cover and an anterior surface of the right eye. A right pressure source, in communication with the right cavity, can be configured to adjust fluid pressure in the right cavity. Control circuitry, coupled to at least one of the left or right pressure sources, can be configured such that the left pressure source is capable of adjusting fluid pressure in the left cavity independently of the right pressure source and the right pressure source is capable of adjusting fluid pressure in the right cavity independently of the left pressure source.

Aspect 2 can include or use or can optionally be combined with the subject matter of Aspect 1 to optionally include or use a left cavity sensor, in communication with the left cavity, to sense an indication of a left eye environment in the left cavity, a right cavity sensor, in communication with the right cavity, to sense an indication of a right eye environment in the right cavity, and a redundant sensor configured to sense at least one of the indication of the left eye environment, the indication of the right eye environment, or an indication of a relationship between the indication of the left eye environment and the indication of the right eye environment.

Aspect 3 can include or use or can optionally be combined with the subject matter of one or any combination of Aspects 1 or 2 to optionally include or use an apparatus wherein the left cavity sensor includes a left pressure sensor to sense an indication of left pressure in the left cavity, the right cavity sensor includes a right pressure sensor to sense an indication of right pressure in the right cavity, and the redundant sensor includes a redundant sensor to sense the indication of the relationship between the indication of the left eye environment and the indication of the right eye environment.

Aspect 4 can include or use or can optionally be combined with the subject matter of one or any combination of Aspects 1 through 3 to optionally include or use an apparatus wherein the redundant sensor includes a differential pressure sensor configured to sense a difference between an indication of left pressure in the left cavity with a left differential pressure sensor and an indication of right pressure in the right cavity with a right differential pressure sensor.

Aspect 5 can include or use or can optionally be combined with the subject matter of one or any combination of Aspects 1 through 4 to optionally include or use the redundant sensor wherein the redundant sensor includes a differential signal sensor configured to sense a difference between an indication of left pressure from the left cavity sensor with a left differential signal sensor and an indication of right pressure from the right cavity sensor with a right differential signal sensor.

Aspect 6 can include or use or can optionally be combined with the subject matter of one or any combination of Aspects 1 through 5 to optionally include or use the system control circuitry wherein the system control circuitry is configured to receive and process at least one of the indication of the left eye environment in the left cavity, the indication of the right eye environment in the right cavity, or the indication of the relationship between the left eye environment and the right eye environment.

Aspect 7 can include or use or can optionally be combined with the subject matter of one or any combination of Aspects 1 through 6 to optionally include or use control circuitry including left control circuitry, coupled to the left pressure source, capable of receiving and processing at least one of the indication of the left eye environment or the indication of the relationship between the left eye environment and the right eye environment and right control circuitry, in communication with the right pressure source, capable of receiving and processing at least one of the indication of the right eye environment or the indication of the relationship between the left eye environment and the right eye environment.

Aspect 8 can include or use or can optionally be combined with the subject matter of one or any combination of Aspects 1 through 7 to optionally include or use left control circuitry wherein the left control circuitry includes the left control circuitry configured to adjust the left pressure source to generate non-ambient pressure in the left cavity toward a left target cavity pressure in the left cavity and right control circuitry wherein the right control circuitry includes the right control circuitry configured to adjust the right pressure source to generate non-ambient pressure in the right cavity toward a right target cavity pressure in the right cavity.

Aspect 9 can include or use or can optionally be combined with the subject matter of one or any combination of Aspects 1 through 8 to optionally include or use a left biosensor, in communication with the left control circuitry, configured to sense at least one of an indication of left intraocular pressure (IOP) in the left eye or an indication of cerebrospinal fluid pressure (CSFP) in the patient and a right biosensor, in communication with the right control circuitry, configured to sense at least one of an indication of right IOP in the right eye or an indication of CSFP in the patient.

Aspect 10 can include or use or can optionally be combined with the subject matter of one or any combination of Aspects 1 through 9 to optionally include or use left control circuitry including the left control circuitry configured to receive the indication of left IOP and adjust the left pressure source to generate non-ambient pressure toward a left target IOP level [G] based on the received indication of left IOP, and right control circuitry including the right control circuitry configured to receive the indication of right IOP and adjust the right pressure source to generate non-ambient pressure toward a right target IOP level based on the received indication of right IOP.

Aspect 11 can include or use or can optionally be combined with the subject matter of one or any combination of Aspects 1 through 10 to optionally include or use left control circuitry wherein the left control circuitry can be configured to generate non-ambient pressure toward the left target IOP level includes the left target IOP level in a range of about 10 mmHg to about 21 mmHg in the left eye, and right control circuitry wherein the right control circuitry can be configured to generate non-ambient pressure toward the right target IOP level includes the right target IOP level in a range of about 10 mmHg to about 21 mmHg in the right eye.

Aspect 12 can include or use or can optionally be combined with the subject matter of one or any combination of Aspects 1 through 11 to optionally include or use left control circuitry including left control circuitry configured to adjust the left pressure source to generate non-ambient pressure in the left cavity to equalize an indication of left translaminar pressure gradient (TLPG) associated with the left eye, wherein equalizing the indication of left TLPG includes reducing the indication of left TLPG from a first left TLPG level to a lower second left TLPG level, and right control circuitry including right control circuitry configured to adjust the right pressure source to generate non-ambient pressure in the right cavity to equalize an indication of right TLPG associated with the right eye, wherein equalizing the indication of right TLPG includes reducing the indication of right TLPG from a first right TLPG level to a lower second right TLPG level.

Aspect 13 can include or use or can optionally be combined with the subject matter of one or any combination of Aspects 1 through 12 to optionally include or use left control circuitry including left control circuitry configured to adjust the left pressure source to generate non-ambient pressure in the left cavity to enhance an indication of axonal transport in the left optic nerve of the left eye and right control circuitry including right control circuitry configured to adjust the right pressure source to generate non-ambient pressure in the right cavity to enhance an indication of axonal transport in the right optic nerve of the right eye, wherein enhancing an indication of axonal transport includes increasing the rate of axonal transport from a first axonal transport level to a greater second axonal transport level.

Aspect 14 can include or use or can optionally be combined with the subject matter of one or any combination of Aspects 1 through 13 to optionally include or use left control circuitry including left control circuitry configured to adjust the left pressure source to generate non-ambient pressure in the left cavity to treat, inhibit, or prevent an eye condition in the left eye and right control circuitry including the right control circuitry configured to adjust the right pressure source to generate non-ambient pressure in the right cavity to treat, inhibit, or prevent an eye condition in the right eye.

Aspect 15 can include or use or can optionally be combined with the subject matter of one or any combination of Aspects 1 through 14 to optionally include or use a left passive cavity check valve, in communication with the left cavity, configured to limit left pressure in the left cavity to a left cracking pressure and a right passive cavity check valve, in communication with the right cavity, configured to limit right pressure in the right cavity to a right cracking pressure.

Aspect 16 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 1 through 15 to optionally include or use a method of using an apparatus. The apparatus can comprise a left cover, sized and shaped to fit over a left eye of a patient to define a left cavity between the left cover and an anterior surface of the left eye, a left pressure source, in communication with the left cavity, configured to adjust fluid pressure in the left cavity, a right cover, sized and shaped to fit over a right eye of the patient to define a right cavity between the right cover and an anterior surface of the right eye, and a right pressure source, in communication with the right cavity, configured to adjust fluid pressure in the right cavity, wherein the left pressure source is configured to adjust fluid pressure in the left cavity independently of the right pressure source and the right pressure source is configured to adjust fluid pressure in the right cavity independently of the left pressure source. The method can include a step of receiving at least one of an indication of a left eye environment, an indication of a right eye environment, an indication of left intraocular pressure (IOP) in the left eye, an indication of right IOP in the right eye, or an indication of cerebrospinal fluid pressure (CSFP) in the patient with the apparatus. The method can include a step of adjusting at least one of the left pressure source to generate non-ambient pressure in the left cavity based on at least one of the received indications or the right pressure source to generate non-ambient pressure in the right cavity based on at least one of the received indications.

Aspect 17 can include or use or can optionally be combined with the subject matter of one or any combination of Aspects 1 through 16 to optionally include or use the method wherein receiving an indication includes receiving an indication of the left eye environment including an indication of left cavity pressure and adjusting the pressure source includes adjusting the left pressure source based on the indication of left cavity pressure and receiving an indication includes receiving an indication of the right eye environment including an indication of right cavity pressure and adjusting the pressure source includes adjusting the right pressure source based on the indication of right cavity pressure.

Aspect 18 can include or use or can optionally be combined with the subject matter of one or any combination of Aspects 1 through 17 to optionally include or use the method wherein receiving an indication includes receiving the indication of left IOP and adjusting the pressure source includes adjusting the left pressure source based on the indication of left IOP and receiving an indication includes receiving the indication of right IOP and adjusting the pressure source includes adjusting the right pressure source based on the indication of right IOP.

Aspect 19 can include or use or can optionally be combined with the subject matter of one or any combination of Aspects 1 through 18 to optionally include or use the method wherein receiving an indication includes receiving the indication of left cavity pressure and left IOP and adjusting the pressure source includes adjusting the left pressure source based on the indication of left cavity pressure and left IOP and receiving an indication includes receiving the indication of right cavity pressure and right IOP and adjusting the pressure source includes adjusting the right pressure source based on the indication of right cavity pressure and right IOP.

Aspect 20 can include or use or can optionally be combined with the subject matter of one or any combination of Aspects 1 through 18 to optionally include or use the method wherein receiving an indication includes receiving an indication of left translaminar pressure difference (TPD) associated with the left eye and adjusting the pressure source includes adjusting the left pressure source to equalize the indication of left TPD and receiving an indication includes receiving an indication of right TPD associated with the right eye and adjusting the pressure source includes adjusting the right pressure source to equalize the indication of right TPD, wherein equalizing the indication of TPD includes reducing the indication of TPD from a first TPD level to a lower second TPD level.

Aspect 21 can include or use subject matter (such as an apparatus, a system, a device, a method, a means for performing acts, or a device readable medium including instructions that, when performed by the device, can cause the device to perform acts), such as an apparatus to adjust fluid pressure applied to at least one of a left cavity located over a left eye of a patient or a right cavity located over a right eye of the patient to treat, inhibit, or prevent an eye condition. The apparatus can include a differential sensor, in communication with the left cavity and the right cavity, configured to sense at least one of an indication of a left eye environment in the left cavity, an indication of a right eye environment in the right cavity, or an indication of a relationship between the indication of the left eye environment and the indication of the right eye environment. The apparatus can include control circuitry, in communication with the system sensor, configured to receive and process at least one of the indication of the left eye environment in the left cavity, the indication of the right eye environment in the right cavity, or the indication of the relationship between the indications of the left eye environment and the right eye environment.

Aspect 22 can include or use or can optionally be combined with the subject matter of Aspect 21 to optionally include or use at least one of a left cavity sensor, coupled to the system control circuitry, to sense an indication of a left eye environment in the left cavity or a right cavity sensor, coupled to the system control circuitry, to sense an indication of the right eye environment in the right cavity.

Aspect 23 can include or use or can optionally be combined with the subject matter of one or any combination of Aspects 21 or 22 to optionally include or use the differential sensor including a differential pressure sensor configured to sense the difference between an indication of left pressure in the left cavity sensed with a left differential pressure sensor and an indication of right pressure in the right cavity sensed with a right differential pressure sensor.

Aspect 24 can include or use or can optionally be combined with the subject matter of one or any combination of Aspects 21 through 23 to optionally include or use the differential sensor including a differential signal sensor configured to sense the difference between an indication of left pressure from a left pressure sensor sensed with a left differential signal sensor and an indication of right pressure from a right pressure sensor sensed with a right differential signal sensor.

Aspect 25 can include or use or can optionally be combined with the subject matter of one or any combination of Aspects 21 through 24 to optionally include or use a pressure source, in communication with at least one of the left cavity or the right cavity, configured to apply non-ambient pressure to at least one of the left cavity or the right cavity.

Aspect 26 can include or use or can optionally be combined with the subject matter of one or any combination of Aspects 21 through 25 to optionally include or use the pressure source including the pressure source configured to apply non-ambient pressure to the left cavity and the right cavity.

Aspect 27 can include or use or can optionally be combined with the subject matter of one or any combination of Aspects 21 through 26 to optionally include or use a left cavity valve, in communication with the left cavity, configured to adjust the indication of left pressure in the left cavity and a right cavity valve, in communication with the right cavity, configured to adjust the indication of right pressure in the right cavity.

Aspect 28 can include or use or can optionally be combined with the subject matter of one or any combination of Aspects 21 through 27 to optionally include or use the left valve including at least one of a passive left valve or an active left valve and the right valve including at least one of a passive right valve or an active right valve.

Aspect 29 can include or use or can optionally be combined with the subject matter of one or any combination of Aspects 21 through 28 to optionally include or use the left cavity valve including the active left cavity valve configured to adjust the indication of left pressure based on at least one of the indications received with the system control circuitry and the right cavity valve including the active right cavity valve configured to adjust the indication of right pressure based on at least one of the indications received with the system control circuitry.

Aspect 30 can include or use or can optionally be combined with the subject matter of one or any combination of Aspects 21 through 29 to optionally include or use a left biosensor, in communication with the system control circuitry, configured to sense at least one of an indication of left intraocular pressure (IOP) in the left eye or an indication of cerebrospinal fluid pressure (CSFP) in the patient and a right biosensor, in communication with the system control circuitry, configured to sense at least one of an indication of right IOP in the right eye or an indication of CSFP in the patient, wherein, the left cavity valve includes the active left cavity valve configured to adjust the indication of left pressure based on at least one of the indications received from the left biosensor and the right cavity valve includes the active right cavity valve configured to adjust the indication of right pressure based on at least one of the indications received from the right biosensor.

Aspect 31 can include or use or can optionally be combined with the subject matter of one or any combination of Aspects 21 through 30 to optionally include or use system control circuitry including left control circuitry configured to receive the indication of left IOP and adjust left pressure in the left cavity with the active left valve toward a left target IOP level based on the received indication of left IOP and right control circuitry configured to receive the indication of right IOP and adjust right pressure in the right cavity with the active right valve toward a right target IOP level based on the received indication of right IOP.

Aspect 32 can include or use or can optionally be combined with the subject matter of one or any combination of Aspects 21 through 31 to optionally include or use left control circuitry configured to adjust left pressure in the left cavity with the left active valve to equalize an indication of left translaminar pressure difference (TPD) associated with the left eye, wherein equalizing the indication of left TPD includes reducing the indication of left TPD from a first left TPD level to a lower second left TPD level, and right control circuitry configured to adjust the right pressure in the right cavity with the right active valve to equalize an indication of right TPD associated with the right eye, wherein equalizing the indication of right TPD includes reducing the indication of right TPD from a first right TPD level to a lower second right TPD level.

Aspect 33 can include or use or can optionally be combined with the subject matter of one or any combination of Aspects 21 through 32 to optionally include or use left control circuitry configured to adjust left pressure in the left cavity with the left active valve sufficient to enhance an indication of axonal transport in the left optic nerve of the left eye and right control circuitry configured to adjust right pressure in the right cavity with the active right valve sufficient to enhance an indication of axonal transport in the right optic nerve of the right eye, wherein enhancing an indication of axonal transport includes increasing the rate of axonal transport from a first axonal transport level to a greater second axonal transport level.

Aspect 34 can include or use or can optionally be combined with the subject matter of one or any combination of Aspects 21 through 33 to optionally include or use system control circuitry including left control circuitry configured to adjust left pressure in the left cavity with the active left valve to treat, inhibit, or prevent an eye condition in the left eye and right control circuitry configured to adjust right pressure in the right cavity with the active right valve to treat, inhibit, or prevent an eye condition in the right eye.

Aspect 35 can include or use or can optionally be combined with the subject matter of one or any combination of Aspects 21 through 34 to optionally include or use a passive left valve, in communication with the left cavity, configured to limit left pressure in the left cavity to a left cracking pressure and a passive right valve, in communication with the right cavity, configured to limit right pressure in the right cavity to a right cracking pressure.

Aspect 36 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 21 through 35 to optionally include or use a method of using an apparatus. The apparatus can comprise a system sensor including a left pressure sensor in communication with a left cavity to sense an indication of left pressure in the left cavity, a right pressure sensor in communication with a right cavity to sense an indication of right pressure in the right cavity and a redundant sensor, system control circuitry, in communication with the system sensor, configured to receive and process at least one of the indication of left pressure or the indication of right pressure, an active left valve in communication with the left cavity and the system control circuitry, and an active right valve in communication with the right cavity and the system control circuitry. The method can include a step of sensing the indication of left pressure in the left cavity and the indication of right pressure in the right cavity with the system sensor. The method can include a step of adjusting at least one of the active left valve based on the sensed indication of left pressure or the active right valve based on the sensed indication of right pressure.

Aspect 37 can include or use or can optionally be combined with the subject matter of one or any combination of Aspects 21 through 36 to optionally include or use a left biosensor, in communication with the system control circuitry, configured to sense at least one of an indication of left intraocular pressure (IOP) in the left eye or an indication of cerebrospinal fluid pressure (CSFP) in the patient, and a right biosensor, in communication with the system control circuitry, configured to sense at least one of an indication of right IOP in the right eye or an indication of CSFP in the patient and the method includes adjusting the at least one of the active left valve or the active right valve includes adjusting at least one of the active left valve based on at least one of the indications received from the left biosensor or the active right valve based on at least one of the indications received from the right biosensor.

Aspect 38 can include or use or can optionally be combined with the subject matter of one or any combination of Aspects 21 through 37 to optionally include or use the method wherein adjusting the at least one of the active left valve or the active right valve includes adjusting at least one of the active left valve to change left pressure toward a left target IOP level based on the received indication of left IOP or the active right valve to change right pressure toward a right target IOP level based on the received indication of right IOP.

Aspect 39 can include or use or can optionally be combined with the subject matter of one or any combination of Aspects 21 through 38 to optionally include or use the method wherein adjusting the at least one of the active left valve or the active right valve includes adjusting at least one of the active left valve to equalize an indication of left translaminar pressure difference (TPD) associated with the left eye or the active right valve to equalize an indication of right TPD associated with the right eye, wherein equalizing the indication of TPD includes reducing the indication of TPD from a first TPD level to a lower second TPD level.

Aspect 40 can include or use or can optionally be combined with the subject matter of one or any combination of Aspects 21 through 39 to optionally include or use the method wherein adjusting the at least one of the active left valve or the active right valve includes adjusting at least one of the active left valve to achieve a left pressure in the left cavity sufficient to enhance an indication of axonal transport in the left optic nerve of the left eye or the active right valve to achieve a right pressure in the right cavity sufficient to enhance an indication of axonal transport in the right optic nerve of the right eye, wherein enhancing an indication of axonal transport includes increasing the rate of axonal transport from a first axonal transport level to a greater second axonal transport level.

Aspect 41 can include or use subject matter (such as an apparatus, a system, a device, a method, a means for performing acts, or a device readable medium including instructions that, when performed by the device, can cause the device to perform acts), such as an apparatus to limit fluid pressure level applied to a left eye and a right eye of a patient. The apparatus can include a pressure source, in communication with a left cavity located over the left eye and a right cavity located over the right eye, configured to adjust an indication of fluid pressure in the left and right cavities. The apparatus can include a differential sensor, in communication with the left cavity and the right cavity, configured to sense at least one of an indication of a left eye environment in the left cavity, an indication of a right eye environment in the right cavity, or an indication of a relationship between the indication of the left eye environment and the indication of the right eye environment.

Aspect 42 can include or use or can optionally be combined with the subject matter of Aspect 41 to optionally include or use at least one of a left cavity sensor, coupled to the left cavity, to sense an indication of a left eye environment in the left cavity or a right cavity sensor, coupled to the right cavity, to sense an indication of the right eye environment in the right cavity.

Aspect 43 can include or use or can optionally be combined with the subject matter of one or any combination of Aspects 41 or 42 to optionally include or use the apparatus wherein the differential sensor includes a differential pressure sensor configured to sense a difference between an indication of left pressure in the left cavity sensed by a left differential pressure sensor and an indication of right pressure in the right cavity sensed by a right differential pressure sensor.

Aspect 44 can include or use or can optionally be combined with the subject matter of one or any combination of Aspects 41 through 43 to optionally include or use the apparatus wherein the differential sensor includes a differential signal sensor configured to sense a difference between an indication of left pressure from a left cavity sensor with a left differential signal sensor and an indication of right pressure from the right pressure sensor with a right differential signal sensor.

Aspect 45 can include or use or can optionally be combined with the subject matter of one or any combination of Aspects 41 through 44 to optionally include or use system control circuitry, in communication the pressure source, configured to receive and process at least one of the indication of the left eye environment in the left cavity, the indication of the right eye environment in the right cavity, or an indication of the relationship between the indication of the left eye environment and the indication of the right eye environment.

Aspect 46 can include or use or can optionally be combined with the subject matter of one or any combination of Aspects 41 through 45 to optionally include or use the apparatus wherein the indication of the left eye environment includes an indication of left pressure in the left cavity, the indication of the right eye environment includes an indication of right pressure in the right cavity, and the indication of the relationship between the left and right eye environments includes an indication of the difference between the indication of the left pressure and the indication of right pressure.

Aspect 47 can include or use or can optionally be combined with the subject matter of one or any combination of Aspects 41 through 46 to optionally include or use system control circuitry including pressure source circuitry configured to adjust operation of the pressure source based on at least one of the received indications.

Aspect 48 can include or use or can optionally be combined with the subject matter of one or any combination of Aspects 41 through 47 to optionally include or use the pressure source circuitry including a pressure source logic circuit configured to generate a system fault based on at least one of the received indications.

Aspect 49 can include or use or can optionally be combined with the subject matter of one or any combination of Aspects 41 through 48 to optionally include or use pressure source circuitry including pressure source circuitry configured to generate the system fault when at least one of the indication of left pressure exceeds a left pressure safety level or the indication of the right pressure exceeds a right pressure safety level.

Aspect 50 can include or use or can optionally be combined with the subject matter of one or any combination of Aspects 41 through 49 to optionally include or use the apparatus wherein the indication of the relationship between the left and right eye environments includes an indication of the difference between the indication of the left pressure and the indication of the right pressure and pressure source circuitry includes pressure source circuitry configured to generate the system fault when the indication of the difference exceeds a differential pressure safety level between the left pressure and the right pressure.

Aspect 51 can include or use or can optionally be combined with the subject matter of one or any combination of Aspects 41 through 50 to optionally include or use a left valve, in communication with the left cavity, configured to limit fluid pressure in the left cavity to a left pressure safety level and a right valve, in communication with the right cavity, configured to limit fluid pressure in the right cavity to a right pressure safety level.

Aspect 52 can include or use or can optionally be combined with the subject matter of one or any combination of Aspects 41 through 51 to optionally include or use the left valve and the right valve wherein at least one of the left pressure safety level or the right safety pressure level are in a range of about −50 mmHg to about 50 mmHg gauge.

Aspect 53 can include or use or can optionally be combined with the subject matter of one or any combination of Aspects 41 through 52 to optionally include or use the left valve and the right valve wherein at least one of the left pressure safety level or the right safety pressure level are in a range of about −35 mmHg to about 35 mmHg gauge.

Aspect 54 can include or use or can optionally be combined with the subject matter of one or any combination of Aspects 41 through 53 to optionally include or use the left valve and the right valve wherein at least one of the left valve or the right valve includes a passive valve.

Aspect 54 can include or use or can optionally be combined with the subject matter of one or any combination of Aspects 41 through 53 to optionally include or use the left valve and the right valve wherein at least one of the left valve or the right valve includes an active valve.

Aspect 56 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 41 through 55 to optionally include or use a method of using an apparatus. The apparatus can comprise a pressure source in communication with a left cavity located over a patient left eye and a right cavity located over a patient right eye and a system sensor including a left cavity sensor to sense an indication of a left eye environment in the left cavity, a right cavity sensor to sense an indication of a right eye environment in the right cavity, and a redundant sensor to sense a relationship between the indication of the left eye environment and the indication of the right eye environment. The method can include a step of sensing an indication of left pressure in the left cavity and an indication of right pressure in the right cavity with the system sensor. The method can include a step of limiting pressure applied to the left cavity and the right cavity by the pressure source.

Aspect 57 can include or use or can optionally be combined with the subject matter of one or any combination of Aspects 41 through 56 to optionally include or use at least one of a left passive valve in communication with the left cavity or a right passive valve in communication with the right cavity and the method wherein limiting pressure includes selecting at least one of a left cracking pressure of the left passive valve or a right cracking pressure of the right passive valve.

Aspect 58 can include or use or can optionally be combined with the subject matter of one or any combination of Aspects 41 through 57 to optionally include or use at least one of a left active valve in communication with the left cavity and a right active valve in communication with the right cavity and the method wherein limiting pressure includes opening at least one of the left active valve or the right active valve based on at least one of the sensed indications of left pressure or right pressure.

Aspect 59 can include or use or can optionally be combined with the subject matter of one or any combination of Aspects 41 through 57 to optionally include or use the method wherein opening at least one of the left active valve or the right active valve includes opening at least one of the left active valve or the right active valve based on the difference between the sensed indications of left and right pressure.

Aspect 60 can include or use or can optionally be combined with the subject matter of one or any combination of Aspects 41 through 57 to optionally include or use the method wherein limiting pressure includes modulating operation of the pressure source based on at least one of the sensed indications of left pressure or right pressure.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
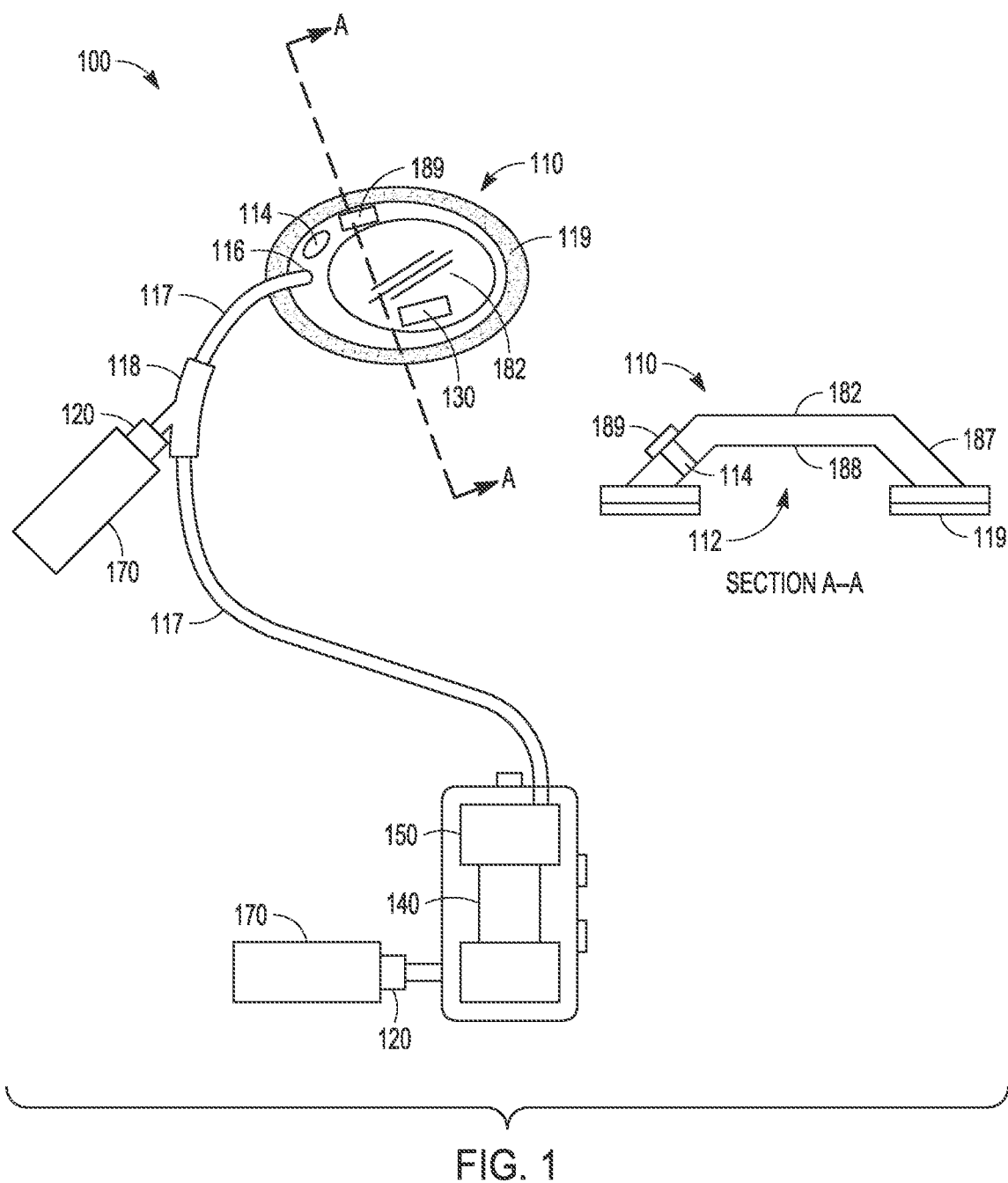
FIG. 1 shows an example of an apparatus, such as to control an environment over a patient eye, in accordance with at least one example of the present disclosure.

FIG. 1 shows an example of an apparatus 100, such as to control an environment over a patient eye. In an example, the patient eye can include an organ of the visual system, a portion of the organ, such as an anterior surface of the patient eye, of the organ and surrounding tissue. The apparatus 100 can include a cover 110, a fluid regulator 120, a sensor 130, control circuitry 140, and a pressure source 150.

The cover 110 can be sized and shaped to surround the patient eye and be spaced from the eye, such as without contacting the eye including the anterior surface of the eye. The cover 110 can be sized and shaped to surround and cover both patient eyes, such as the left eye and the right eye of a patient. In an example, the cover 110 can include a mask, such as a cover 110 similar in shape and function to a diving or snorkeling mask. The cover 110 can include a lens portion 182, such as to allow a patient to see outward through the cover 110 or to allow observation of the eye, such as exterior structures of the eye including the cornea or intraocular structures of the eye including the retina, inward through the cover 110. The lens portion 182 can serve as a corrective lens for the patient, such as to correct an astigmatism of the eye. The lens portion 182 can include a lens blank, such as an A8 lens blank, that can be shaped as a prescription lens for the patient. The lens portion 182 can include a replaceable lens portion 182, such as a first lens portion in the apparatus 100 can be interchanged with a second lens portion, such as to change the lens magnification presented to the patient. The inner surface of the lens portion 182 can be treated, such as with an anti-fog coating to prevent condensation from obscuring the view of the patient.

The cover 110 can define an enclosed cavity 112, such as when the cover 110 is placed over the eye and against the patient. The cavity 112 can define an enclosed cavity 112 over both eyes, such as when the cover 110 includes a mask located over left and right patient eyes. In an example, the cavity 112 can define a spatial volume, such as the spatial volume defined between an inner surface 188 of the cover 110 and an anterior surface of the patient eye. The cavity 112 can contain a working fluid, such as a liquid or gaseous fluid, that can form an eye environment in contact with the patient eye. In an example, the eye environment can be used to characterize a physiological state of the patient eye, such as the eye environment can include physiological constituents including biomarkers emitted from the eye. Information sensed by the apparatus 100, such as biomarkers sensed from the working fluid in the cavity 112, can provide a medical professional with patient information, such as to diagnosis an eye condition associated with the patient eye. In an example, the eye environment can be used to treat a patient eye, such as the apparatus 100 can adjust the eye environment to vary at least one of pressure in the cavity 112 or the working fluid composition to treat an eye condition.

An eye condition can describe a state of an eye, such as a physiological state of the eye that can affect the vision of a patient. An eye condition can include at least one of an acute eye condition, such as an eye condition that can persist for a period of time measured in seconds, minutes, or days, or a chronic eye condition, such as an eye condition that can persist for a period of time measured in days, weeks, months, or years. In an example, an eye condition can include an abnormal eye condition, such as an eye experiencing a disease state. A disease state of the eye can include at least one of glaucoma, papilledema, such as optic disk edema, Fuchs dystrophy, diabetic retinopathy, macular degeneration, such as wet or dry macular degeneration, cataract, dry eye, corneal infection, meibomian gland disease, demodex, corneal ectasia, or periocular skin laxity.

The eye condition can be affected by the apparatus 100, such as by exposing the patient eye, including the anterior portion of the eye, to the eye environment in the cavity 112. In an example, glaucoma can be treated, inhibited, or prevented with the apparatus 100, such as by exposing the eye to an eye environment including a negative gauge pressure. In an example, optic disk edema can be treated, inhibited, or prevented with the apparatus 100, such as by exposing the eye to an eye environment including a positive gauge pressure. In an example, an aerobic eye infection can be treated, inhibited, or prevented with the apparatus 100, such as by exposing the eye to an anerobic environment (e.g., an environment without oxygen), such as to address the underlying cause of the aerobic eye infection.

One or more eye conditions can be affected by the apparatus 100, such as simultaneously affected, by exposing the eye to the environment in the cavity 112. In an example, where a patient can experience one or more eye conditions, such as glaucoma and an aerobic eye infection, the eye conditions can be treated, inhibited, or prevented with the apparatus 100, such as by exposing the patient eye to an eye environment including a negative gauge pressure anerobic eye environment, such as the negative pressure environment to treat glaucoma and the anerobic environment to treat the aerobic eye infection.

The eye environment can be defined by an indication of a working fluid characteristic, such as an indication of the working fluid characteristic in the cavity 112. The working fluid characteristic can include at least one of working fluid flow in the cavity 112, such as working fluid volumetric flow rate including at least one of volumetric flow rate into or out of the cavity 112, working fluid humidity in the cavity 112, such as the relative humidity of the working fluid in the cavity 112, working fluid temperature in the cavity 112, working fluid pressure in the cavity 112, such as the working fluid gauge pressure in the cavity 112 including the pressure difference between the working fluid pressure in the cavity and the ambient pressure of the environment surrounding the cavity, or working fluid composition in the cavity 112, such as working fluid composition measured by at least one of constituent fluid concentration or partial fluid pressure.

The cover 110 can retain the working fluid against the patient, such as in contact with the anterior portion of the patient eye to form an eye environment in the cavity 112. Exposure of the patient eye to the eye environment can affect a treatment of the eye, such as at least one of a diagnostic treatment of the eye, such as a diagnostic test, or a therapeutic treatment of the eye, such as to treat, inhibit or prevent an eye condition associated with the eye. In an example, treatment of the eye can include exposure of the eye to at least one of the working fluid pressure in the cavity 112, such as to apply a force to the anterior portion of the eye, or exposure of the eye to the working fluid composition in the cavity 112, such as a working fluid composed of one or more constituent fluids, such as including one or more therapeutic fluids.

The cover 110 can maintain a gauge pressure in the cavity 112, such as a differential fluid pressure between the working fluid in the cavity and the surrounding atmosphere. In an example, gauge pressure can be defined as the difference in pressure between the working fluid pressure in the cavity 112 and atmospheric pressure surrounding the cover 110. A positive gauge pressure, such as where working fluid pressure in the cavity 112 is greater than atmospheric pressure, can create a compressive working fluid force on the anterior surface of the eye, such as to increase intraocular pressure (IOP) in the eye. A negative gauge pressure, such as where working fluid pressure in the cavity 112 is less than atmospheric pressure, can create a negative (or "vacuum") working fluid force on the anterior surface of the eye, such as to decrease IOP in the eye.

The working fluid force applied to the anterior surface of the eye can include a perturbation force, such as a force for a diagnostic test that can be applied to the anterior surface of the eye for a period of time sufficient to allow for measurement of the deflection of the eye from a first position to a second position. In an example, application of a perturbation force for a period measured in seconds or minutes can be sufficient for deflection measurement. The perturbation force can be generated by a positive gauge pressure in the cavity 112 to exert a positive perturbation force on the eye, such as to decrease the curvature of the eye for a diagnostic test including a diagnostic measurement. The perturbation force can be generated by a negative gauge pressure in the cavity 112 to exert a negative perturbation force on the eye, such as to increase the curvature of the eye for a diagnostic test including a diagnostic measurement.

The force applied to the anterior surface of the eye can include a therapeutic force, such as a force to apply a therapy regimen to the anterior surface of the eye for a period of time sufficient to treat an eye condition including an acute eye condition or a chronic eye condition. In an example, application of a therapeutic force for a period measured in days, weeks, months, or years can be applied depending on the eye condition treated. The therapeutic force can be generated by a positive gauge pressure to exert a positive therapeutic compressive force on the eye, such as to increase the intraocular pressure (or IOP) of the eye to inhibit, treat, or prevent an eye condition including optic disc edema. The therapeutic force can be generated by a negative gauge pressure that can exert a negative therapeutic force on the eye, such as to decrease the IOP of the eye to inhibit, treat, or prevent an eye condition including glaucoma.

The working fluid can be composed of one or more constituent fluids, such as a combination of one or more liquids or gases. A working fluid can include a combination of two constituent fluids, such as a combination of gaseous nitric oxide and gaseous carbon dioxide. A constituent fluid can include a therapeutic fluid, such as a component of the constituent fluid can be absorbed through the eye to inhibit, treat, or prevent an eye condition. For example, a working fluid can include a combination of nitrogen and nitric oxide, such as the nitric oxide constituent can be absorbed through a surface of the eye to promote vasodilation of blood vessels in the eye to treat an eye condition including glaucoma.

A therapeutic fluid can include a gaseous therapeutic fluid, such as carbon dioxide ($CO_2$), oxygen ($O_2$), nitric oxide (NO), ozone ($O_3$), nitrogen ($N_2$), helium (He), hydrocarbons including fluorocarbons and perfluorocarbons, sulfur hexafluoride, cannabinoids including tetrahydrocannabinol (THC) and cannabidiol (CBD), a combination of two or more gaseous therapeutic fluids, or the like. In an example, a therapeutic gas can include a mixture of at least one of carbon dioxide, oxygen, or nitric oxide, such as to treat an eye condition. In an example, a therapeutic gas can include a mixture of nitric oxide and oxygen including a mixture of 50% nitric oxide and 50% oxygen, a mixture of helium and oxygen (also known as heliox), and Medical Air including Medical Grade Air USP. In an example, a mixture of therapeutic gases can include a mixture of nitric oxide and oxygen, such as a mixture of 50% nitric oxide and 50% oxygen including gases from The BOC Group plc under the tradename ENTONOX, such as to treat an eye condition. In an example, a combination of therapeutic gases can include a mixture of helium and oxygen, such as a mixture of 21% oxygen and 79% helium, also known as heliox, such as to treat an eye condition. In an example, a combination of therapeutic gases can include a mixture of at least one of fluorine or chlorine, such as to treat an eye condition including an eye infection. In an example, a combination of therapeutic gases can include at least one of a mixture with a volume fraction of oxygen less than ambient air, such as the mixture with less than about twenty-one percent volume fraction $O_2$, such as to treat an aerobic eye infection, or a mixture with a volume fraction of oxygen greater than ambient air, such as the mixture with more than about twenty-one percent volume fraction $O_2$, such as to treat an anaerobic eye infection.

A therapeutic fluid can include a liquid therapeutic fluid, such as a therapeutic solution. The therapeutic solution can include a solvent, such as water ($H_2O$), and a solute, such as a therapeutic solute. The therapeutic solute can include at least one of vitamin A, B vitamins, such as riboflavin (vitamin B2), Vitamin C, Vitamin D, Vitamin E, beta-caotene, zinc, leutein, or folate. The therapeutic solution can be converted from a liquid therapeutic fluid to a gaseous therapeutic fluid, such as with a nebulizer or an atomizer to form a therapeutic mist or fog, for delivery to the cavity 112 and contact with the patient eye. In an example, a patient eye can be exposed to a gaseous therapeutic fluid, such as a therapeutic mist including Vitamin A, to achieve a first therapeutic result, such as treatment of a corneal ulcer. In an example, a patient eye can be exposed to a gaseous therapeutic fluid, such as a therapeutic mist including riboflavin, and subsequently exposed to potentiating energy, such as ultraviolet light, to achieve a second therapeutic result, such as increased corneal cross-linking to treat keratoconus.

The cover 110 can include a first port 114. The first post 114 can be located in a surface of the cover 110, such as the first port 114 can extend from an outer surface 187 of the cover 110 to an inner surface 188 of the cover 110 to allow access to the eye environment in the cavity 112. The first port 114 can include a septum, such as a flexible septum located over the first port 114 to isolate the cavity 112 from the surrounding environment. The flexible septum can maintain a gauge pressure, such as at least one of a positive or negative gauge pressure, in the cavity 112.

The flexible septum can include a resealable septum, such as a septum formed from a self-healing material including a self-sealing polymer material that can allow the insertion and withdrawal of instruments through the septum into the cavity 112 while maintaining a gauge pressure in the cavity 112. In an example, the resealable septum can allow a hypodermic needle to be inserted and withdrawn through the resealable septum while maintaining a gauge pressure (e.g. a positive or negative gauge pressure) in the cavity 112. For example, the resealable septum can allow for a hypodermic needle to be placed in proximity of the eye, such as to place a therapeutic fluid in contact with the eye, while maintaining a gauge pressure in the cavity 112.

The flexible septum can include a measurement septum, such as a septum to allow a sensor, such as the sensor 130, to sense an indication of the eye environment in the cavity 112 without contacting the eye environment. In an example, a pressure sensor can be located in contact with the measurement septum covering the first port 114 of the cover 110, such as to sense an indication of working fluid pressure in the cavity 112 through the pressure measurement septum.

The cover 110 can include a second port 116, extending from an outer surface 187 of the cover 110 to an inner surface 188 of the cover 110. In an example, the second port 116 can place the cavity 112 in communication with the pressure source 150, such as with a conduit 117.

The cover 110 can include a seal 119, such as to provide an interface including a cover-patient interface between the cover 110 and the patient to improve patient comfort when wearing the apparatus 100. The seal can also serve as a barrier, such as to separate the eye environment in the cavity 112 from the surrounding environment. The seal 119 can attach to the periphery of the cover 110, such as at least a portion of the periphery of the cover 110. In an example, the seal 119 can extend continuously around the periphery of the cover, such as to form a sealing surface between the cover 110 and the patient 119 to separate the volume of the cavity 112 from the surrounding environment.

The apparatus 100 can include a cavity check valve 189. The cavity check valve 189 can be located on the apparatus 100 in communication with the cavity 112, such as on at least one of the cover 110 including any surface of the cover 110, the conduit 117, the control circuitry 140, or the pressure source 150. In an example, the cavity check valve 189 can be located in proximity to, such as in, on, or over, the first port 114.

The cavity check valve 189 can limit the working fluid pressure applied to the cavity 112. In an example, the cavity check valve 189 can be used as a safety valve, such as to ensure that pressure in the cavity 112 will not exceed cavity pressure levels that could damage the eye. In an example, the cavity check valve 189 can limit pressure in the cavity 112 to a target cavity pressure level.

The cavity check valve 189 can include a cracking pressure, such as a characteristic of the cavity check valve 189 that can control initiation of fluid flow through the valve. In an example, the cracking pressure can describe an inlet pressure level of the cavity check valve 189 at which a fluid can initiate flow through the cavity check valve 189. Working fluid pressure in the cavity 112 can be limited to the target cavity pressure level by selecting or setting the cracking pressure of the cavity check valve 189, such as by selecting or setting the cracking pressure of the cavity check valve 189 to equal the target cavity pressure level.

The cavity check valve 189 can include a passive cavity check valve, such as a flapper valve or a poppet valve. The cracking pressure of the passive cavity check valve can be adjusted, such as by changing the dimensions of the passive cavity check valve or components of the passive cavity check valve. In an example, the cracking pressure of a flapper cavity check valve can be adjusted, such as by changing at least one of the flapper check valve dimensions (e.g., length, width, thickness), the flapper check valve constituent material (e.g. type of material, durometer of material, single or multi-ply material, stiffness of valve), or the flapper check valve hinge. In an example, the cracking pressure of a poppet cavity check valve can be adjusted, such as by changing at least one of the poppet valve dimensions (e.g., spring stiffness, poppet diameter).

Figure 2A:
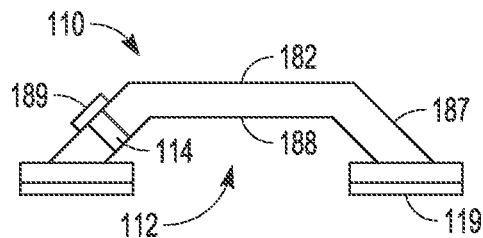
FIGS. 2A and 2B show a side view of an example of a positive pressure cavity check valve in a closed and open position, in accordance with at least one example of the present disclosure.
Figure 2B:
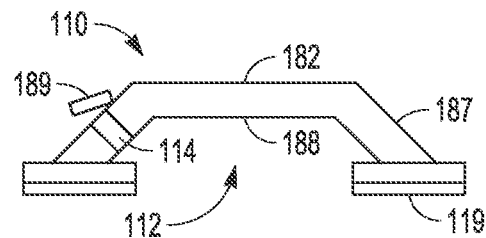

FIGS. 2A and 2B show a side view of an example of a positive pressure cavity check valve, such as a flapper valve configured to control pressure in the cavity 112 to a positive target cavity pressure level. The positive target cavity pressure level can be specified, such as by a medical professional to treat, inhibit, or prevent an eye condition. The positive pressure cavity check valve can be located on the cover 110, such as the outer surface 187 of the cover 110 to allow positive pressure working fluid to flow from the cavity 112 to the surrounding environment.

As shown in FIG. 2A, the cavity check valve 189 can assume a closed position, such as working fluid cannot pass from the cavity 112 through the cavity check valve 189 to the surrounding environment. In the closed position, the apparatus 100 can support a positive gauge pressure environment in the cavity 112, such as a positive gauge pressure level less than the positive target cavity pressure level. The positive target cavity pressure level can be controlled, such as by setting the cracking pressure of the positive pressure cavity check valve to equal the positive target cavity pressure level.

As shown in FIG. 2B, the cavity check valve 189 can assume an open position, such as working fluid can pass from the cavity 112 through the cavity check valve 189 to the surrounding environment, such as when the positive gauge pressure in the cavity 112 is equal to or greater than the positive target cavity pressure level. In the open position, the apparatus 100 can limit the positive gauge pressure environment in the cavity 112 to a pressure level approximately equal to the positive target cavity pressure level, such as to protect the eye from excessive working fluid pressure.

Figure 3A:
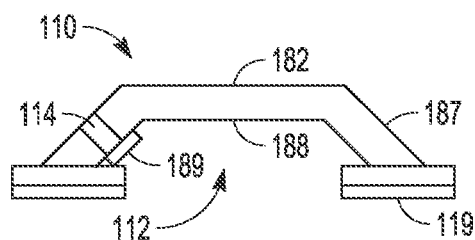
FIGS. 3A and 3B show a side view of an example of a negative pressure cavity check valve in a closed and open position, in accordance with at least one example of the present disclosure
Figure 3B:
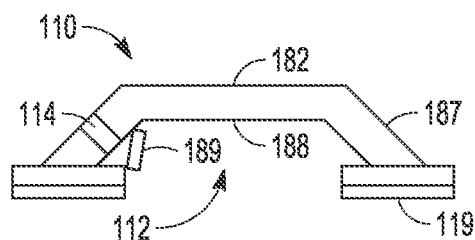

FIGS. 3A and 3B show a side view of an example of a negative pressure cavity check valve, such as a flapper valve configured to control pressure in the cavity 112 to a negative target cavity pressure level. The negative target cavity pressure level can be specified, such as by a medical professional to treat, inhibit, or prevent an eye condition. The negative pressure cavity check valve can be located on the cover 110, such as the inner surface 188 of the cover 110 to allow fluid from the surrounding environment to flow into the cavity 112 from the surrounding environment.

As shown in FIG. 3A, the cavity check valve 189 can assume a closed position, such as ambient fluid cannot pass into the cavity 112 through the cavity check valve 189 from the surrounding environment. In the closed position, the apparatus 110 can support a negative gauge pressure environment in the cavity 112, such as a negative gauge pressure level greater than the negative target cavity pressure level. The negative target cavity pressure level can be controlled, such as by setting the cracking pressure of the negative pressure cavity check valve to equal the negative target cavity pressure level.

As shown in FIG. 3B, the cavity check valve 189 can assume an open position, such as ambient fluid can pass into the cavity 112 through the cavity check valve 189 from the surrounding environment, such as when the negative gauge pressure in the cavity 112 is equal to or less than the negative target cavity pressure level. In the open position, the apparatus 100 can limit the negative gauge pressure environment in the cavity 112 to a pressure level approximately equal to the negative target cavity pressure level, such as to prevent possible damage to the eye by excessive working fluid pressure.

As the patient eye condition changes, such as improves or degrades, a medical professional can adjust the prescribed treatment regimen, such as to change at least one of the positive target cavity pressure level or the negative target cavity pressure level. The apparatus 100 can include a check valve assembly 190, such as a replaceable check valve assembly 190 to adjust the target cavity pressure level in the cavity 112. In an example, the apparatus 100 with a first check valve assembly including a first cavity check valve with a first cracking pressure set to a first target pressure level, can be replaced with a second check valve assembly including a second cavity check valve with a second cracking pressure set to a second target pressure level, such as to realize a change in a prescribed patient treatment regimen including a change in target cavity pressure level.

Figure 4:
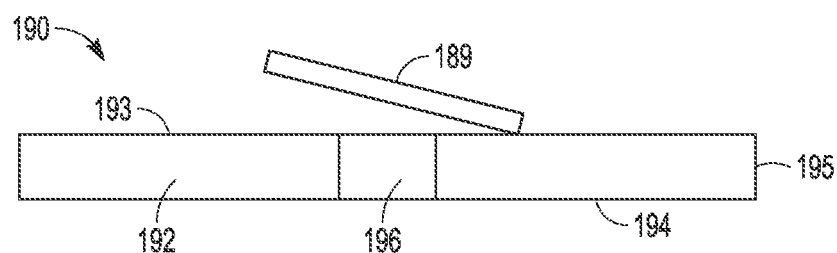
FIG. 4 shows an example of a check valve assembly, in accordance with at least one example of the present disclosure.

FIG. 4 shows a side view of an example of a check valve assembly 190, such as a flapper check valve assembly in an open position. The cavity check valve assembly 190 can include a base 192 with a first side 193, a second side 194 parallel to the first side 193, a base periphery 195 extending from the first side 193 to the second side 194, a base port 196 extending through the base 192 from the first side 193 to the second side 194, and a cavity check valve 189 located on the first side 193 over the base port 196, such as at least a portion of the base port 196.

The check valve assembly 190 can be located on the apparatus 100 in communication with the cavity 112, such as on at least one of the cover 110 including any surface of the cover 110, the conduit 117, the control circuitry 140, or the pressure source 150. The cavity check valve assembly 190 can be located in contact with the cover 110, such as the base periphery 195 can be in contact with at least a portion of the cover 110, such as at least one of the surface of the port 114, the outer surface 187, or the inner surface 188. The cavity check valve assembly 190, such as a positive pressure check valve assembly, can be configured to control pressure in the cavity 112 to a positive target cavity pressure level, such as the check valve assembly 190 can be located in the port 114 so that the cavity check valve 189 can be located outside of the cavity 112. The cavity check valve assembly 190, such as a negative pressure check valve assembly, can be configured to control pressure in the cavity 112 to a negative target cavity pressure level, such as the check valve assembly 190 can be located in the port 114 so that the cavity check valve 189 can be located inside the cavity 112.

Referring again to FIG. 1, the fluid regulator 120 can regulate the flow of fluid between two reservoirs, such as the fluid flow between the cavity 112 and a fluid source 170, such as a pressurized gas cylinder. The fluid regulator 120 can include a regulator valve, such as to regulate flow rates between the first and second reservoirs. The regulator valve can include a passive valve, such as a check valve that closes as pressure exceeds a critical value. In an example, a fluid regulator 120 with a check valve can be located between the cover 110 and a fluid source 170, such as if the pressure of the fluid source 170 exceeds a critical value, such as a pressure that can cause damage to a patient eye, the check valve can close to isolate pressure of the fluid source 170 from the patient eye, such as to protect the patient eye from excessive force. The regulator valve can include an active valve, such as an electrically-modulated valve including a servo valve, or a proportional valve, such as a piezo-actuated proportional valve. In an example, the regulator valve can receive a control signal, such as from the control circuitry 140, to modulate the position of the electrically-modulated spool with respect to the valve body, such as to regulate fluid flow through the electrically-modulated valve.

The fluid regulator 120 can attach to a fluid source 170, such as to regulate the flow of fluid from the fluid source 170 to the cavity 112. The fluid source 170 can include a fluid vessel, such as a storage container of pressurized gaseous fluid. The fluid source 170 can include a generator device, such as a device that concentrates or distills a constituent fluid from another fluid. In an example, a generator device can include a concentrator, such as an oxygen concentrator or a carbon dioxide concentrator. In an example, a generator device can include an atomizer, such as an ultrasonic humidifier or an aerosolizer, to transform a liquid therapeutic fluid, such as a miscible solution or colloidal suspension, into a gaseous working fluid, such as a therapeutic mist or fog.

The fluid regulator 120 can communicate with apparatus 100, such as the fluid regulator 120 can communicate with the cavity 112. In an example, the fluid regulator 120 can be connected to the cover 110, such as with the conduit 117 in direct communication with the cover 110 through the second port 116. In an example, the fluid regulator 120 can be connected to the conduit 117 in communication with the cover 110 by a tube connector 118, such as a Y-connector. In an example, the fluid regulator 120 can be connected to the control circuitry 140, such as to receive a control signal from the control circuitry 140 to adjust the position of a servo valve.

The sensor 130 can sense an indication of the eye environment in the cavity 112, such as at least one of an indication of a characteristic of the working fluid in the cavity 112 or an indication of a physiological parameter of the patient. The sensor 130 can include sensor circuitry, such as sensor circuitry to receive an indication of a physical parameter sensed by the sensor 130 and process the received indication, such as into an indication including an electrical signal suitable to be received by at least one of the control circuitry 140 or the pressure source 150.

The sensor 130 can be located in proximity to the apparatus 100, such as in communication with the cavity 112 or at least partially attached to the patient. In an example, the sensor 130 can be separate from the apparatus 100. For example, the sensor 130 can include a handheld pressure gauge, such as to be pressed against a measurement septum located over the port 114 to sense an indication of working fluid pressure in the cavity 112. In an example, the sensor 130 can be in fluidic communication with the cavity 112, such as the sensor 130 can be located in the cavity 112 or on the control circuitry 140 in fluidic communication with the cavity 112. In an example, the sensor 130 can be at least partially attached to the patient, such as to a surface of the eye including an anterior surface of the eye or patient tissue covering the skull including tissue over the frontal, parietal, sphenoid, temporal, zygomatic, maxillary, occipital, and mandibular bones. For example, the sensor 130 can include an electroretinography device, such as part of which can include an electrode attached to patient tissue to sense an indication of electrical activity in the patient including electrical activity associated with a pattern electroretinography (or PERG) test. The sensor 130 can be in electrical communication with the apparatus, such as at least one of the control circuitry 140 or the pressure source 150. The sensor 130 can provide at least one of continuous or periodic (e.g. intermittent) sensing of the working fluid, such as for monitoring an indication of the eye environment with the sensor 130, or an indication of the physiological parameter associated with the patient, such as IOP or CSFP.

The sensor 130 can include a flow sensor, such as a device to sense an indication of working fluid flow including at least one of volumetric flow rate or mass flow rate into or out of the cavity 112. The sensor 130 can include a humidity sensor, such as a device to sense an indication of the relative humidity of the working fluid in the cavity 112. The sensor 130 can include a thermometer, such as a device to sense an indication of the temperature of the working fluid in the cavity 112. The sensor 130 can include a displacement sensor, such as a device to sense an indication of displacement including an optical coherence tomography device configured to sense displacement of structures associated with the patient eye.

The sensor 130 can include a pressure sensor, such as a device to sense an indication of working fluid pressure in the cavity 112. The pressure sensor can be located in proximity to the cavity 112, such as in communication with the cavity 112. In an example, the pressure sensor can be located in the cavity 112.

Static cavity pressure level in the cavity 112, such as the pressure level sensed by the pressure sensor when the pressure source 150 is not adjusting working fluid pressure in the cavity 112, can be the same at any location in the cavity 112. Dynamic cavity pressure level, such as the pressure level sensed by the pressure sensor when the pressure source 150 is adjusting working fluid pressure in the cavity 112, can vary depending on the location of the pressure sensor in communication with the cavity 112.

The sensor 130 can include a pressure sensor in combination with another indication, such as an indication of the operating state of the pressure source 150, to estimate a static cavity pressure level in the cavity 112. In an example, the pressure sensor, such as a pressure-flow sensor including a sensor that can measure both working fluid pressure (static and dynamic) and working fluid flow at a measurement location, can be located in proximity to the pressure source 150, such as an inlet port or an outlet port of the pressure source 150, to sense an indication of dynamic pressure at the pressure sensor location and include circuitry, such as sensor circuitry to receive an indication of the operation state of the pressure source 150 including an indication of flow rate (e.g., pump speed can be proportional to flow rate). The pressure-flow sensor can process at least one of the indication of dynamic pressure or the indication of flow rate, such as to form a control signal that can be received by the pressure source 150 to achieve a static cavity pressure level, such as a target pressure level, in the cavity 112. The control signal can be based on a relationship between the indication of dynamic pressure and the indication flow rate, such as a relationship between pressure and flow including the relationship described by a p-Q (e.g., pressure-flow) chart that can account for the operating characteristics of the pressure source 150.

In an example, the pressure sensor can be located in proximity to the pressure source 150. The control circuitry 140 can be configured to receive an indication of dynamic pressure from the pressure sensor and an indication of the operation state of the pressure source 150 including an indication of pump speed. The control circuitry 140 can process at least one of the indication of dynamic pressure or the indication of pressure source 150 operation state, such as to form a control signal that can be received by the pressure source 150 to achieve a static cavity pressure level, such as a target pressure level, in the cavity 112.

The sensor 130 can include a concentration sensor, such as a device to sense an indication of a chemical constituent in the working fluid. In an example, the concentration sensor can be configured to sense an indication of a therapeutic fluid, such as at least one of ($CO_2$), oxygen ($O_2$), nitric oxide (NO), ozone ($O_3$), nitrogen, helium (He), hydrocarbons including fluorocarbons and perfluorocarbons, sulfur hexafluoride, cannabinoids including tetrahydrocannabinol (THC) and cannabidiol (CBD), or a combination of therapeutic gases.

The sensor 130 can include a biomarker sensor, such as a device to sense an indication of a biomarker in the working fluid including a biomarker released from the patient eye or sensed within the patient eye. A biomarker can suggest a physiological state of the eye, such as a state of distress where medical intervention can be required. The biomarker sensor can include a volatile gas sensor including a quartz crystal nanobalance (QCN) sensor, such as to sense an indication of a ketone in the working fluid. The biomarker sensor can include a glucose sensor including an ocular coherence tomography (OCT) imaging system, such as to sense an indication of glucose level in the patient. The biomarker sensor can include an oxygen sensor including a non-invasive optical oxygen sensor, such as to sense an indication of oxygen in the patient eye or the working fluid. The biomarker sensor can include a salinity sensor, such as to sense an indication of dissolved salt in the patient eye or the working fluid. The biomarker sensor can include an aptamer-based sensor, such as to sense an indication of vascular endothelial growth factor (or VEGF) in the patient eye or in the working fluid. The biomarker sensor can include an enzyme sensor, such as to detect an enzyme including a matrix metallopeptidase 9 (MPP-9) enzyme in the patient eye or in the working fluid. The biomarker sensor can include a protein sensor, such as to detect a protein including a brain-derived neurotrophic factor (BDNF) protein in the patient eye or in the working fluid.

The sensor 130 can include a biosensor, such as a sensor configured to sense an indication of a physiological parameter associated with a patient. A physiological parameter can include an indication of a physiological process associated with the patient, such as a process associated with a patient eye or process associated with physiological activity of the patient eye. In an example, a physiological parameter can include at least one of an indication of intraocular pressure (IOP) in the patient eye, such as an IOP level, an indication of cerebrospinal fluid pressure (CSFP) associated with the patient, such as a CSFP level, an indication of cardiac activity, such as at least one of systemic blood pressure or heart rate. A physiological parameter can include an indication of retinal activity, such as measured by an electroretinography device including a pattern electroretinography (or PERG) device.

The control circuitry 140 can facilitate and coordinate operation of the apparatus 100. In an example, the control circuitry 140 can be coupled to, such as in communication with, at least one of the fluid regulator 120, the sensor 130, the pressure source 150, or the fluid source 170.

The control circuitry 140 can include a data interface configured to receive a signal, such as at least one of an indication of the eye environment sensed by the sensor 130. In an example, a sensed indication can include at least one of an indication of the eye environment or an indication of a relationship between an indication of a left eye environment and an indication of a right eye environment, such as the sensed indication from the sensor 130. The control circuitry 140 can process the received signal, such as into a processed signal, and transmit the processed signal to one or more components of the apparatus 100. The control circuitry 140 can be in communication with the fluid regulator 120, such as to adjust the position of the regulator valve to control the working fluid composition. The control circuitry 140 can be in communication with the sensor 130, such as to receive and process an indication of the eye environment including sensed data from the sensor 130. The control circuitry 140 can be in communication with the pressure source 150, such as to adjust at least one of working fluid pressure or working fluid flow in the apparatus 100.

The control circuitry 140 can provide a communication interface, such as to allow for a user to operate and interact with the apparatus 100. The communication interface can include a graphical user interface (or GUI), such as communicate information to the user including information on the apparatus 100 (e.g., readout of sensed indications, fault status, etc) or receive information from the user. Information received from the user can include at least one of information to manage basic functionality of the apparatus 100, such as cycling the power to the apparatus 100, or an indication of user preference, such as operational parameters including target levels to define therapeutic protocols and safety parameter such as maximum and minimum limits. In an example, the communication interface can receive a safety pressure level, such as at least one of a maximum or minimum pressure level in the cavity 112 selected by the user to prevent damage to the patient eye.

The control circuitry 140 can include a data acquisition unit (or DAC) to monitor and record an indication, such as an indication of the eye environment sensed by the sensor 130. The indication of the eye environment can be monitored and recorded by the control circuitry 140 for a period of time, such as for a period of seconds, minutes, hours, days, years, or for the lifetime of the patient.

The control circuitry 140 can include a processing unit, such as a programmable central processing unit (CPU). The CPU can execute instructions to implement methods of using the apparatus 100, such as to treat, inhibit, or prevent a patient eye condition. In an example, the CPU can be a component of a computing machine, such as a computing machine 1500.

The CPU can be configured as a control circuit, such as a feedback control circuit. The feedback control circuit can receive information, such as at least one of an indication sensed by the sensor 130, an indication of user preference from the communication interface, or an indication of a processed signal including a signal processed by the CPU, and process the sensed indication, such as to form a control signal.

The CPU can be configured as a pressure feedback control circuit, such as to generate a control signal for the pressure source 150 (e.g., a pressure source control signal) to adjust pressure level in the cavity 112, such as based on an indication of cavity pressure level from a pressure sensor in communication with the cavity 112.

In an example, the pressure source control signal can be based on an indication of cavity pressure, such as pressure in the cavity 112, to achieve a target pressure level in the cavity 112. The pressure feedback control circuit can receive an indication of working fluid pressure in the cavity 112, such as an indication of cavity pressure level sensed by the sensor 130 including a pressure sensor in communication with the cavity 112. The pressure feedback control circuit can process the received indication of pressure level to form a control signal, such as a control signal to adjust the pressure source 150 to achieve the target pressure level in the cavity 112.

Processing the received indication of pressure can include calculating an indication, such as calculating an indication of the difference between the indication of cavity pressure level and an indication of user preference, including a cavity pressure setpoint level received from the communication interface to form an indication of a cavity pressure difference value. Processing the received indication can include generating a control signal based on the indication of cavity pressure difference value with a proportional-integral-derivative (PID) control algorithm running on the CPU to adjust the pressure source 150. Generating a control signal can include generating a control signal to minimize the difference between the received indication of pressure level and the cavity pressure setpoint level.

In an example, the pressure source control signal can be based on an indication of a physiological parameter associated with the patient, such as an indication of IOP in the patient eye, to achieve a target IOP level in the patient eye. The pressure feedback control circuit can receive an indication of IOP level in the patient eye, such as an indication of IOP level sensed by the sensor 130 including a biosensor configured to sense IOP. The pressure feedback control circuit can process the received indication of IOP level to form a control signal, such as a control signal to adjust the pressure source 150, to achieve a target cavity pressure level in the cavity 112, such as a target cavity pressure level sufficient to achieve the target IOP level in the patient eye.

Processing the received indication of IOP can include calculating the difference between the indication of IOP level and an indication of user preference, including an IOP setpoint level received from the communication interface, to form an IOP difference value. Processing the received indication can include generating a control signal based on the IOP difference value with a proportional-integral-derivative (PID) control algorithm running on the CPU to adjust the pressure source 150. Generating a control signal can include generating a control signal to minimize the difference between the received indication of pressure level and the cavity pressure setpoint level.

The CPU can be configured as a concentration feedback control circuit, such as to generate a regulator control signal to adjust a chemical constituent level in the cavity 112.

In an example, the regulator control signal can be based on an indication of a chemical constituent associated with the working fluid, such as an indication of nitric oxide (NO) concentration, to achieve a target NO concentration level in the working fluid. The concentration feedback control circuit can receive an indication of NO concentration level in the working fluid, such as an indication of NO level sensed by the senor 130 including a concentration sensor configured to sense NO. The concentration feedback control circuit can process the received indication of NO level to form a control signal, such as a control signal to adjust the regulator 120 to achieve the target NO concentration level in the cavity 112.

Processing the received indication of NO concentration can include calculating the difference between the indication of NO concentration and an indication of user preference, including a NO setpoint level received from the communication interface, to form a NO difference value. Processing the received indication can include generating a control signal based on the NO difference value. Processing the received indication can include generating a control signal based on the NO difference value with a proportional-integral-derivative (PID) control algorithm running on the CPU to adjust the regulator 120. Generating a control signal can include generating a control signal to minimize the difference between the received indication of NO concentration and the NO setpoint level.

The control circuitry 140 can include pressure source circuitry, such as pressure source circuitry configured to adjust operation of the pressure source 150 based on at least one of an indication sensed by the sensor 130. The pressure source circuitry can include a pressure source logic circuit, such as a pressure source logic circuit configured to generate a system fault based on at least one of a sensed indication received at the data interface or an indication of user preference received through the communication interface. In an example, the pressure source logic circuit can generate a system fault on the occurrence of a fault event, such as when an indication of cavity pressure in the in the cavity 112 exceeds a pressure safety level, such as a pressure safety level set by a user through the communication interface.

The control circuitry 140 can include a power source, such as to supply electrical energy to the apparatus 100. In an example, the power source can include a battery, such as a lithium ion battery, and a transformer, such as to receive power from a wall outlet for use in the apparatus 100 at a specified voltage and current. The control circuitry 140 can include a heating element, such as a heating element in communication with the therapeutic fluid including a heating element located on a surface of the cover 110 including an inner surface 188 of the cover 110, to increase the temperature of the therapeutic fluid.

The pressure source 150 can be configured to generate a volumetric fluid flow in the apparatus 100, such as to move working fluid from the pressure source 150 to the cavity 112 or to move working fluid from the cavity 112 to at least one of the pressure source 150 or to the surrounding environment. The pressure source 150 can be configured to apply non-ambient pressure to the cavity 112, such as to adjust an indication of fluid pressure including an indication of pressure level in the cavity 112, from a first pressure level to a second pressure level different from the first pressure level.

The pressure source 150 can include a pump, such as a pump that can generate at least one of a positive gauge pressure or a negative gauge pressure. The pressure source 150 can include an electrically-powered pressure source, such as a pump including a displacement pump or a centrifugal pump. For example, a pressure source 150 can include a diaphragm vacuum pump. The pressure source 150 can include a manually-powered pressure source, such as a hand pump including a bellows-style pump. In an example, the pressure source 150 can be integrated into a component of the apparatus 100, such as the cover 110.

Figure 1A:
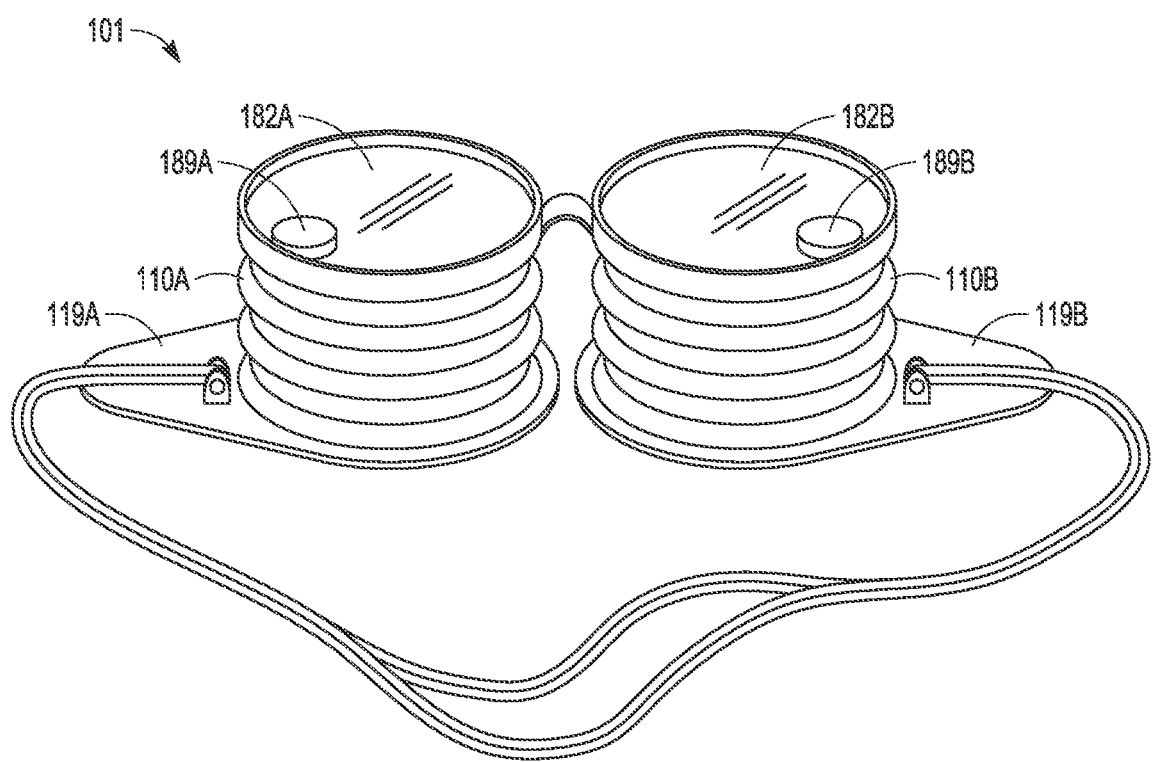
FIG. 1A shows an example of an apparatus including an example of a manually-powered pressure source, in accordance with at least one example of the present disclosure.

FIG. 1A shows an example of an apparatus 101 including an example of a manually-powered pressure source. In an example, the apparatus 101 can include all the components of the apparatus 100. The apparatus 101 can include a bellows cover 111, such as at least one of a left bellows cover 111A or a right bellows cover 111B, a cavity check valve 189, such as at least one of a left cavity check valve 189A or a right cavity check valve 189B, and a seal 119, such as at least one of a left seal 119A or a right seal 119B.

The bellows cover 111 can be sized and shaped to surround the patient eye and be spaced from the eye, such as without contacting the eye including the anterior surface of the eye. The bellows cover 111 can be sized and shaped to surround and cover both patient eyes, such as the left eye and the right eye of the patient. In an example, the bellows cover 111 can include a mask, such as the bellows cover 111 similar in shape and function to a diving or snorkeling mask.

The bellows cover 111 can include a bellows portion, such as a portion of the bellows cover 111 between the lens 182 and the seal 119. The bellows portion can assume a first bellows position, such as defined by a first bellows distance between the lens 182 and the seal 119. The bellows portion can assume a second bellows position, such as position displaced from the first bellows position. The bellows portion can display a resistance to motion, such as an external force can be required to displace the bellows portion from the first bellows position to the second bellows position. The level of resistance to motion can be controlled, such as through design of the bellows portion including selection of bellows material and number of bellows folds. The bellows portion can display a resilience, such as a tendency of the bellows portion to recover to an equilibrium position including a force equilibrium position after the removal of the external force.

The second bellows position can include a compressed bellows position, such as to generate a negative gauge pressure (e.g., a vacuum) over the patient eye. In an example, the distance between the lens 182 and the seal 119 can be reduced from the first bellows position on the application of a compressive force to the bellows cover 111, such as to the compressed bellows position. As the bellows cover 111 moves from the first bellows position to the compressed bellows position, the volume of the cavity 112 can be reduced, such as to increase working fluid pressure in the cavity 112, after which the cavity 112 can expel a volume of working fluid from the cavity 112, such as through the check valve 189. On removal of the compressive force, the bellows portion can recover to a third bellows position, such as a position between the first and compressed bellows positions, due to the resilience of the bellows portion, such as to create a "suction" or negative gauge pressure over the patient eye.

The second bellows position can include an extended bellows position, such as to generate a positive gauge pressure (e.g., an increase in pressure as compared to ambient pressure) over the patient eye. In an example, the distance between the lens 182 and the seal 119 can be increased from the first bellows position on the application of an extension force to the bellows cover 111, such as to the extended bellows position. As the bellows cover 111 moves from the first bellows position to the extended bellows position, the volume of the cavity 112 can be increased, such as to decrease working fluid pressure in the cavity 112, after which the cavity 112 can receive a volume of ambient air from the surrounding environment, such as through the check valve 189. On removal of the extension force, the bellows portion can recover to a third bellows position, such as a position between the first and extended bellows position, due to the resilience of the bellows portion, such as to create a "pressurized" or positive gauge pressure over the patient eye.

The pressure source 150 can include a source of pressure, such as a pressurized gas cylinder or a source of pressurized fluid separate from the apparatus 100 that can be used to adjust working fluid pressure in the cavity 112. The pressure source 150 can include a source of pressure used in combination with a supplementary device to adjust pressure in the cavity. In an example, the pressure source 150 can include a venturi-type pump, such as a venturi jet pump, in communication with the source of pressure to adjust fluid pressure in the cavity 112.

The pressure source 150 can be characterized by physical characteristics, such as a relationship between physical characteristics. A useful measure for comparing the performance of several sources of flow includes a volume-pressure characteristic, such as the relationship between the volume of working fluid flow from a source of flow and the pressure, such as static pressure, created due to the fluid flow. In an example, the pressure source 150 can be characterized by a volume-pressure characteristic, such as a p-Q chart.

The pressure source 150 can generate a pressure in the cavity 112, such as to adjust pressure in the cavity 112 to move towards or achieve a target cavity pressure in the cavity 112. The target cavity pressure can include the cavity pressure to affect a measurement procedure including a diagnostic procedure on the patient eye. In an example, pressure in the cavity 112 can be adjusted with the pressure source 150 towards a target cavity pressure, such as a first target cavity pressure to affect a first displacement of an anterior surface of the patient eye. An indication of the first displacement can be sensed by a sensor 130 including a displacement sensor. Subsequently, a second target cavity pressure can affect a second displacement of the anterior surface of the patient eye, such as an indication of the second displacement that can be sensed by the displacement sensor. The difference between the indications of displacement at the first and second target pressure can result in an estimate of a physiological parameter, such as an estimate of an indication of IOP in the patient eye.

The target cavity pressure can include the cavity pressure to affect a treatment of the patient eye, such as a cavity pressure prescribed by a medical professional to treat, inhibit, or prevent an eye condition. In an example, pressure in the cavity 112 can be adjusted with the pressure source 150 toward a target cavity pressure, such as a target cavity pressure to affect an indication of a physiological parameter of the patient eye including an indication of IOP level in the patient eye that can be sensed by a sensor 130 including a biosensor configured to sense an indication of IOP. Treatment of the patient eye can be affected by the pressure source 150, such as by adjusting the pressure source to achieve a target cavity pressure in the cavity 112 to affect a desired indication of IOP level in the patient eye.

The target cavity pressure can include a target IOP cavity pressure, such as a pressure applied to the cavity 112 to achieve a target IOP level in the patient eye. A target IOP cavity pressure can include a cavity pressure that can adjust or achieve an IOP level in a patient eye, such as to increase or decrease the IOP level in the patient eye. A target IOP level can include an IOP level in a range about 5 mmHg to about mmHg, an IOP level in a range of about 10 mmHg to about 21 mmHg, and an IOP level in a range of about 12 mmHg to about 18 mmHg.

Translaminar pressure describes the pressure differential across the lamina cribrosa. The translaminar pressure difference (TPD) can be defined as the difference between intraocular pressure in the patient eye and cerebrospinal fluid pressure in the patient body. Translaminar pressure gradient (TPG) is related to TPD and can be defined as the difference between IOP and CSFP per unit thickness of the lamina cribrosa. An indication of TPD, such as TPD level, can indicate the physiological health of the patient eye, such as the presence or absence of an eye condition. A physiologically normal eye, such as a patient eye in the absence of an eye condition, can be characterized by a normal TPD level, such as normal TPD level in a range of about −4 mmHg to about 4 mmHg. In contrast, a non-normal eye, such as a patient eye experiencing an eye condition including glaucoma, can be characterized by a TPD level that falls outside the range of normal TPD level, such as the TPD level can be less than about −4 mmHg or greater than about 4 mmHg.

The target cavity pressure can include a target equalization cavity pressure, such as the pressure applied to the cavity 112 that can equalize TPD level in an eye. A cavity pressure that can equalize TPD level in the eye can include any pressure applied to the cavity 112 that can reduce TPD level in the eye, such as from a first TPD level to a second TPD level including where the absolute value of the second TPD level can be less than the absolute value of the first TPD level.

The target cavity pressure can include a target translaminar pressure difference (TPD) cavity pressure, such as a pressure applied to the cavity 112 that can achieve a target TPD level in the patient eye. A target TPD cavity pressure can include the pressure level applied to the cavity 112 sufficient to adjust the TPD level of a patient eye into a range, such as a target TPD level range. A target TPD level range can include a TPD level in a range of at least one of about −4 mmHg to about 4 mmHg, a TPD level in a range of about −7 mmHg to about 7 mmHg, or a TPD level in a range of about −10 mmHg to about 10 mmHg. In an example, a normal TPD level range can include a TPD level in a range of about −4 mmHg to about 4 mmHg.

Adjusting TPD, such as adjusting TPD in the patient eye from a first TPD level to a second TPD level lower than the first TPD level, can improve physiological processes in the patient eye, such as to improve the health of the patient eye. Axonal transport, such as the collection of cellular processes responsible for maintaining cell viability in the patient optic nerve, can be adversely affected in the presence of elevated TPD, such as where the indication of TPD in the patient eye does not fall within the normal TPD level range. Indications of axonal transport level, such as in the optic nerve, can be sensed by the sensor 130 including an axonal transport sensor. In an example, an axonal transport sensor can include at least one of an optical coherence tomography (OCT) imaging system or a confocal scanning laser ophthalmoscope (CSLO) system.

The target cavity pressure can include a target axonal transport cavity pressure, such as a cavity pressure applied to the cavity 112 to achieve a target axonal transport level in the patient eye. A target axonal transport cavity pressure can include a cavity pressure that can enhance (or increase) an indication of axonal transport level in an eye, such as from a first indication of axonal transport level to a second indication of axonal transport level where the indication of second axonal transport level can be greater than the indication of first axonal transport level.

Rates of axonal transport can vary, such as based on the physiological constituents transported. In an example, "slow" axonal transport can represent the movement of cytoplasmatic constituents along an axon, such as including cytoskeletal and soluble enzymes of intermediary metabolism. A target axonal transport level, such as for slow axonal transport constituents, can include an axonal transport level in a range of about 0.2 mm/day to about 2 mm/day. In an example, "fast" axonal transport can represent the movement of mitochondrial polypeptides and neuropeptides, such as synaptic vesicle polypeptides, along an axon. A target axonal transport level, such as for fast axonal transport constituents, can include an axonal transport level in a range of about 50 mm/day to about 100 mm/day, such as for mitochondrial polypeptides, and an axonal transport level in a range of about 100 mm/day to about 200 mm/day, such as for neuropeptides.

A target cavity pressure can include a target therapeutic cavity pressure to treat, inhibit, or prevent an eye condition in the patient eye.

A target therapeutic cavity pressure to treat an eye condition can include a cavity pressure selected to adjust an indication of a physiological parameter, such as a physiological parameter sensed by the sensor 130. In an example, adjusting an indication of a physiological parameter can include relieving a patient symptom, such as relieving patient discomfort, or improving patient function, such as patient function degraded due to an eye condition or a disease state.

A target therapeutic cavity pressure to inhibit an eye condition can include a cavity pressure selected to maintain patient function, such as to stop or delay further degradation of patient function due to a diagnosed eye condition. In an example, maintaining an indication of patient function can include minimizing variation in an indication of a physiological parameter of the patient eye. For example, a target therapeutic cavity pressure to inhibit an eye condition can include a cavity pressure selected to minimize variation in an indication of IOP over a period of time.

A target therapeutic cavity pressure to prevent an eye condition can include a cavity pressure selected as a prophylactic measure applied to a patient eye prior to the appearance of an eye condition. In an example, for a patient presenting with a precursor characteristic for an eye condition, such as an abnormal cup-to-disc ratio as a potential indication of glaucoma, a cavity pressure can be applied to the patient eye with the apparatus 100, such as at a pressure level suitable for the patient physiology, to prevent physiological processes from progressing to a clinical eye condition diagnosis. Thus, a target cavity pressure level can include a cavity pressure level sufficient to adjust the cup-to-disc ratio in a patient eye from a first cup-to-disc ratio to a second cup-to-disc ratio lower than the first cup-to-disc ratio, such as to reduce the cup-to-disc ratio in the patient eye.

The conduit 117 can provide a patent fluidic transmission path between one or more components of the apparatus 100, such as a continuously patent fluidic transmission path between at least one of the cavity 112 and the sensor 130 or the cavity 112 and the pressure source 150. The conduit 117 can include a lumen, such as one or more lumens.

Figure 5A:
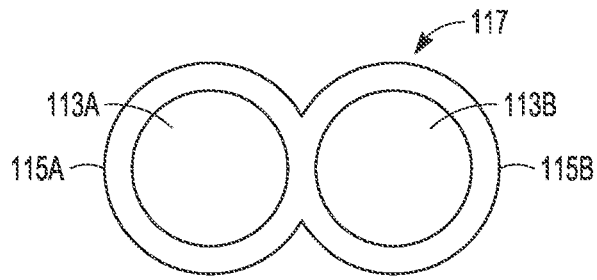
FIG. 5A shows an example of a conduit, such as a first dual lumen conduit, in accordance with at least one example of the present disclosure.

FIG. 5A shows a cross-section of an example of a conduit 117, such as a first dual lumen conduit. The first dual lumen conduit can include a first lumen 113A defined by a first lumen wall 115A and a second lumen 113B defined by a second lumen wall 115B, such as the first lumen 115A can be located adjacent to the second lumen 115B. In an example, the first lumen 113A can provide a fluid communication path between the pressure source 150 and the cavity 112, such as the pressure source 150 can transfer working fluid to the cavity 112 through the lumen 113A to achieve a target cavity pressure level. In an example, the second lumen 113B can provide a fluidic communication path between the cavity 112 and the sensor 130, such as the working fluid pressure sensor located on the control circuitry 140, to allow the sensor 130 to sense an indication of cavity pressure level in the cavity 112, such as for use as a feedback signal to control operation of the pressure source 150.

A potential operational hazard of the apparatus 100 can include a blockage in the conduit 117, such as a state of the conduit 117 where the patent fluidic transmission path can be interrupted, including a kink in the conduit 117. In an example, a kink can include a blockage, such as a blockage due to a bending force applied to the conduit 117 that can cause at least one of the first lumen 113A or the second lumen 113B to fold over and collapse on itself, such as a first portion of an inner surface of the lumen can contact a second portion of the inner surface of the lumen to prevent fluid transmission through the lumen. A kink in the conduit 117 between the cavity 112 and the sensor 130, such as the working fluid pressure sensor located on the control circuitry 140, can create a potential for the pressure source 150 to run out of control, such as the control circuitry 140 can command the pressure source 150 to generate a cavity pressure level based on an erroneous indication of cavity pressure level from the sensor 130.

In an example, a kink in the first lumen 113A can stop fluidic communication between the cavity 112 and the working fluid pressure sensor, such as to cause the working fluid pressure sensor to sense an erroneous indication of cavity pressure level including a state of no cavity pressure level (e.g., an indication of cavity pressure level of about 0 mmHg gauge). The erroneous indication of cavity pressure level can cause the control circuitry 140 to command the pressure source 150 to adjust, such as increase or decrease, fluid transfer to the cavity 112, such as to operate the pressure source 150 to compensate for cavity pressure level in the cavity 112, such as to achieve or maintain the target cavity pressure level. Continued sensing of the erroneous indication of cavity pressure level can cause the pressure source 150 to operate in a "run-away" (or uncontrolled) state, such as to potentially generate cavity pressure levels that could damage the patient eye. To avoid a run-away state, the conduit 117 can include a feature, such as one or more features, designed to enhance the safety of the apparatus 100, such as the operational safety of the apparatus 100 due to a blockage in the conduit 117.

Figure 5B:
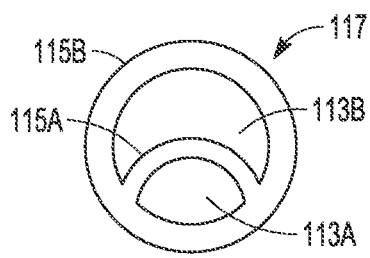
FIG. 5B shows an example of a conduit, such as a second dual lumen conduit, in accordance with at least one example of the present disclosure.

FIG. 5B shows a cross-section of an example of a second dual lumen conduit, such as a conduit 117 where the first lumen wall 115A can interface with the second lumen wall 115B, such as to form a first lumen 113A and a second lumen 113B within the second lumen wall 115B.

Figure 5C:
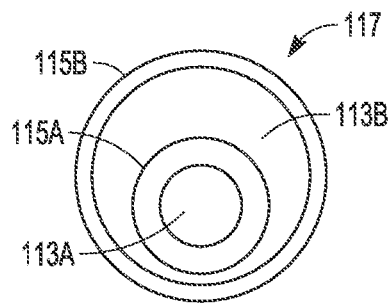
FIG. 5C shows an example of a conduit, such as a third dual lumen conduit, in accordance with at least one example of the present disclosure.

FIG. 5C shows an example of a third dual lumen conduit, such as a conduit 117 where the first lumen 113A can be located completely within the second lumen 113B, such as the first lumen wall 115A can be separate from the second lumen wall 115B.

Patency of the conduit 117 can be controlled, such as by orientation of the first lumen 113A with respect to the second lumen 113B. In an example, a kink in the conduit 117, such as at least one of the example conduit 117 shown in FIG. 5B or FIG. 5C, can block the first lumen 113A, such as to prevent fluid transfer from the pressure source 150 to the cavity 112, but allow the second lumen 113B to remain open, such as an outer surface of the first lumen wall 115A can prevent the second lumen 113B from collapsing on itself, such as by preventing a first portion of the inner surface of the second lumen 113B from contacting a second portion of the inner surface of the second lumen 113B.

Patency of the conduit 117 can be controlled, such as by design of the conduit 117, including design of at least one of the first lumen 113A or the second lumen 113B. Dimensions of conduit 117 can be selected, such as to maintain patency of the second lumen 113B. In an example, the thickness of the first lumen wall 115A can be different from the thickness of the second lumen wall 115B, such as to prevent a first portion of the second lumen 113B from collapsing on itself, such as when subjecting the conduit 117 to a bending force. Materials used to construct the conduit 117 can be selected, maintain patency of the second lumen 113B. In an example, the type or durometer of the material used to form the first lumen wall 115A can be different from the type or durometer of the material used to form the second lumen wall 115B, such as to prevent a first portion of the second lumen 113B from collapsing on itself, such as when subjecting the conduit 117 to a bending force.

The conduit 117 can include a reinforcing structure, such as to prevent blockage of at least one of the first lumen 113A or the second lumen 113B. The reinforcing structure can include a coil of wire, such as a wire coil located in the first lumen wall 115A or the second lumen wall 115B and extending around the periphery of at least one of the first lumen wall 115A or the second lumen wall 115B.

The cross-sectional shape of the conduit 117 can assume any shape without affecting the function of the conduit 117. The cross-sectional shape of the conduit 117, such as the cross-sectional shape of the first lumen 113A and the cross-sectional shape of the second lumen 113B, can include at least one of a circular, oval, crescent, triangular, rectangular, or any polygonal cross-section shape.

Flexibility of the conduit 117, such as the overall stiffness of the conduit 117 due to the stiffness of the first lumen wall 115A and the second lumen wall 115B, can be controlled. In an example, a structural configuration of the conduit 117, such as a structural configuration that minimizes a moment of inertia associated with the cross-sectional shape of the conduit 117, can reduce the stiffness of the conduit 117. For example, a first dual lumen conduit, such as with a first moment of inertia, can demonstrate higher overall stiffness, such as in bending or in torsion, when compared to at least one of a second dual lumen conduit with a second moment of inertia or a third dual lumen conduit with a third moment of inertia, such as where the first moment of inertia can be greater than the second or third moments of inertia. In an example, the second dual lumen conduit or the third dual lumen conduit can minimize torsional bias, such as torsional bias that can result from at least one of bonding or extruding, as compared with the first dual lumen conduit.

Figure 6:
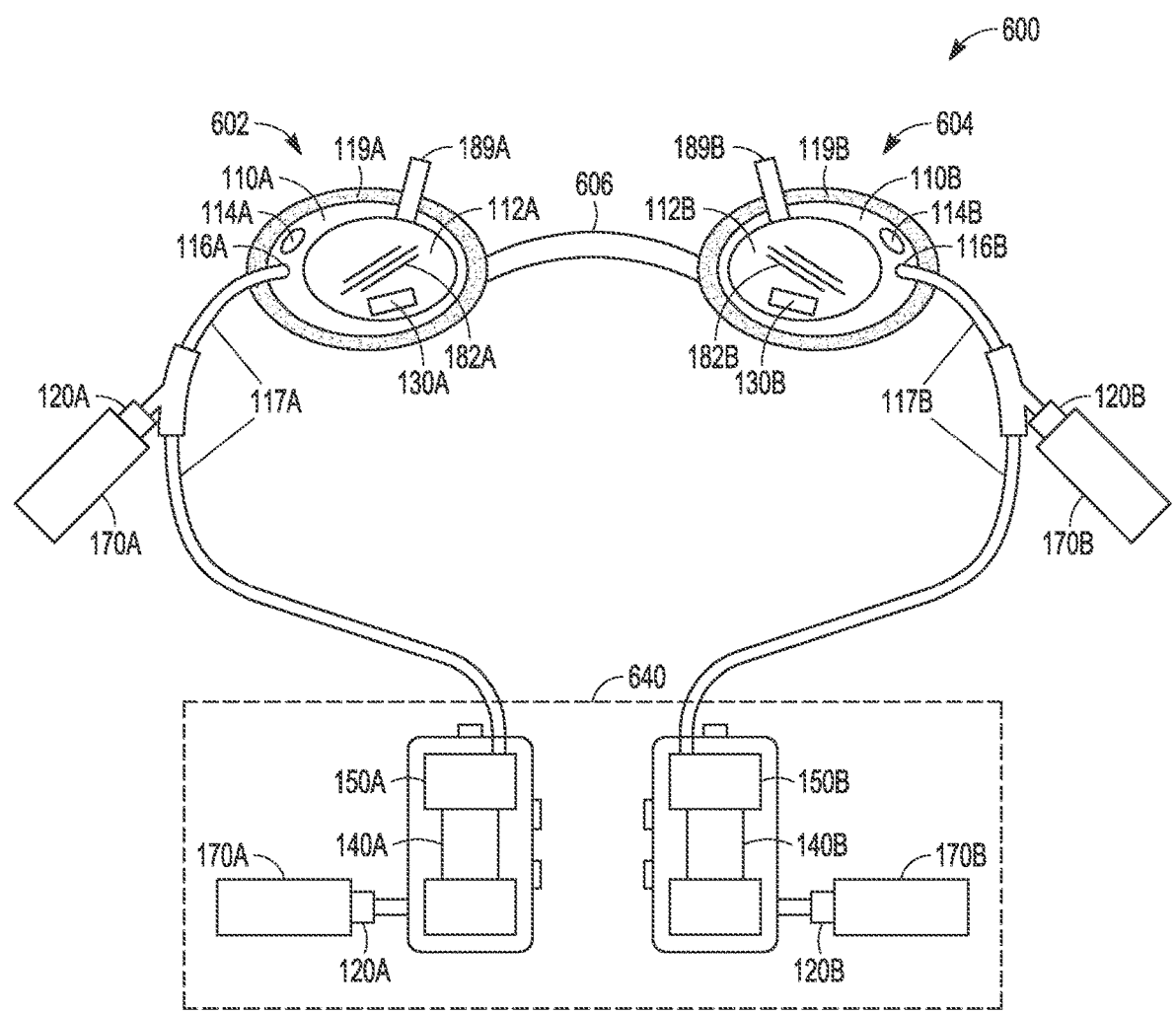
FIG. 6 shows an example of an apparatus that can control a left eye environment over a left eye of a patient and a right eye environment over a right eye of the patient, in accordance with at least one example of the present disclosure.

FIG. 6 shows an example of an apparatus 600 that can control an eye environment over a patient eye, such as at least one of a left eye environment over the left patient eye or a right eye environment over the right patient eye. Controlling an eye environment can include at least one of establishing, adjusting, or maintaining an indication of the eye environment over the patient eye, such as an indication of working fluid cavity pressure in the cavity 112. In an example, control of the left eye environment can be independent of the right eye environment and control of the right eye environment can be independent of the left eye environment.

The apparatus 600 can include a left system 602 with a left cover 110A sized and shaped to fit over a left eye of a patient to define a left cavity 112A between the left cover 110A and an anterior surface of the left eye, a right system 604 with a right cover 110B sized and shaped to fit over the right eye of the patient to define a right cavity 112B between the right cover 110B and an anterior surface of the right eye, and a bridge 606, such as to locate the left system 602 with respect to the right system 604. In an example, the left system 602 can include at least one of the apparatus 100 and the right system 604 can include at least one of the apparatus 100.

The apparatus 600 can include system control circuitry 640 to facilitate, coordinate, and control operation of the apparatus 600. The system control circuitry 640 can be configured to receive and process an indication of the eye environment, such as at least one of an indication of the left eye environment, an indication of the right eye environment, or an indication of a relationship between the indication of the left eye environment and the indication of the right eye environment.

The system control circuitry 640 can include at least one of left control circuitry 140A, such as left control circuitry 140A to facilitate, coordinate, and control operation of the left system 602, or right control circuitry 140B, such as right control circuitry 140B to facilitate, coordinate, and control operation of the right system 602. In an example, the left control circuitry 140A can be configured to control operation of the left system 602 independently of the right system 604 and the right system 604 can be configured to control operation of the right system 604 independently of the left system 602. In an example, the left control circuitry 140A can be capable of receiving and processing at least one of the indication of the left eye environment or the indication of the relationship between the left eye environment and the right eye environment. In an example, the right control circuitry 140B can be capable of receiving and processing at least one of the indication of the right eye environment or the indication of the relationship between the left eye environment and the right eye environment.

The system control circuitry 640 can include pressure source circuitry, such as pressure source circuitry configured to adjust operation of the pressure source based on at least one of the indication of the left eye environment, the indication of the right eye environment, or the indication of a relationship between the indication of the left eye environment and the right eye environment. In an example, the pressure source circuitry can include at least one of left pressure source circuitry, such as coupled to the left control circuitry 140A, or right pressure source circuitry, such as coupled to the right control circuitry 140B.

The pressure source circuitry can include a pressure source logic circuit, such as a pressure source logic circuit configured to generate a system fault based on at least one of the received indications, such as indications received by the system control circuitry 640. In an example, the pressure source logic circuit can generate the system fault on the occurrence of a fault event, such as at least one of an indication of left pressure in the in the left cavity 112A exceeds a left pressure safety level or an indication of right pressure in the right cavity 112B exceeds a right pressure safety level. In an example, the pressure source logic circuit can generate the system fault when the relationship between the indication of the left eye environment and the indication of the right eye environment exceed a "relationship safety level". For example, the pressure source logic circuit can generate the system fault with the difference between the indication of the pressure in the left cavity 112A and the indication of the pressure in the right cavity 112B exceed a relationship safety pressure level. The relationship safety pressure level can be defined by a user, such as through the communication interface associated with the control circuitry 140.

The system control circuitry 640 can be configured to facilitate, coordinate, and control operation of the apparatus 600, such as in a master-slave control configuration. In an example, a first control circuitry can receive and process an indication of the eye environment and a second control circuitry, in communication with the first control circuitry, can receive the processed indication from the first control circuitry and adjust operation of the apparatus 600, such as at least one of the left system 602 or the right system 604. In an example, the first control circuitry can include the left control circuitry 140A and the second control circuitry can include the right control circuitry 140B. In an example, the first control circuitry can include the right control circuitry 140B and the second control circuitry can include the left control circuitry 140A.

In an example, the left control circuitry 140A can control the cavity pressure in the left cavity 112A, such as by adjusting the left pressure source 150A to achieve a target cavity pressure in the cavity 112A. For example, the left control circuitry 140A can be configured to include a control mechanism, such as a feedback control mechanism based on an indication of a physiological parameter from the left sensor 130A, such as an indication of IOP level in the left eye sensed by the left biosensor, and process the received physiological parameter, such as to adjust the left pressure source 150A, to achieve a target cavity pressure level in the left cavity 112A based on the received physiological parameter, such as the received indication of left IOP level.

In an example, the left control circuitry 140A can control the left working fluid composition in the left cavity 112A, such as by adjusting the left fluid regulator 120A to achieve a target fluid composition in the left cavity 112A. For example, the left control circuitry 140A can receive an indication of the left eye environment from the left sensor 130A, such as an indication of nitric oxide (NO) level in the left cavity sensed by the left NO concentration sensor, and process the received indication of the left eye environment, such as to adjust the left fluid regulator 120A, to achieve a target fluid concentration level in the cavity 112A based on the received physiological parameter, such as the received indication of NO level in the left cavity 112A.

The right control circuitry 140B can facilitate, coordinate, and control operation of the right system 604 including the right eye environment in the right cavity 112B independently of the left control circuitry 140A.

For example, the right control circuitry 140B can control at least one cavity pressure in the right cavity 112B, such as by adjusting the right pressure source 150B to achieve a target cavity pressure in the cavity 112B, or the right working fluid composition, such as by adjusting the right fluid regulator 120B to achieve a target fluid composition in the cavity 112B.

The apparatus 600 can control the left eye environment in the left cavity 112A separately from the right eye environment in the right cavity 112B and the right eye environment in the right cavity 112B separately from the left eye environment in the left cavity 112A. In an example, the left system 602 can control at least one of the left cavity pressure or the left working fluid concentration in the left cavity 112A independently of the right system 604 and the right system 604 can control at least one of the right cavity pressure or the right working fluid concentration in the right cavity 112B independently of the left system 602.

The left eye environment can include a left cavity pressure, such as sensed by a left pressure sensor 130A through a left conduit 117A, in the left cavity 112A. The right eye environment can include a right cavity pressure, such as sensed by a right pressure sensor 130B through a right conduit 117B, in the right cavity 112B.

In an example, the left pressure source 150A can control, such as establish, adjust, and maintain, a left cavity pressure in the left cavity 112A. For example, the left pressure source 150A and the left fluid regulator 120A can communicate with the left cavity 112A, such as through the second left port 116A, to generate a left positive gauge pressure in the left cavity 112A, such as to carry a constituent fluid from the left fluid regulator 120A into the left cavity 112A. A left cavity check valve 189A in communication with the left cavity 112A can be configured to limit left cavity pressure within the left cavity 112A, such as to a target left cavity pressure level including a target positive left cavity pressure level or a target negative left cavity pressure level.

In an example, the right pressure source 150B can control, such as establish, adjust, and maintain, a first right cavity pressure in the right cavity 112B. For example, the right pressure source 150B and the right fluid regulator 120B can communicate with the right cavity 112B, such as through the second right port 116B, to generate a right positive gauge pressure in the right cavity 112B, such as to carry a constituent fluid from the right fluid regulator 120B into the right cavity 112B. A right cavity check valve 189B in communication with the right cavity 112B can be configured to limit right cavity pressure within the right cavity 112B, such as to a target right cavity pressure level. In an example, the first left cavity pressure can be adjusted, such as increased or decreased, independently of the right pressure source 150B and the first right cavity pressure can be adjusted, such as increased or decreased, independently of the left pressure source 150A.

The left eye environment can include a left working fluid composition in the left cavity 112A and the right eye environment can include a right working fluid composition in the right cavity 112B. In an example, the left fluid regulator 120A can control a first left working fluid composition in the left cavity 112A. In an example, the right fluid regulator 120B can control, such as establish and maintain, a first right working fluid composition in the right cavity 112B. In an example, the first left working fluid composition can be adjusted, such as a concentration of a constituent of the first left working fluid can be increased or decreased, independently of the right fluid regulator 120B and the first right working fluid composition can be adjusted, such as a concentration of a constituent of the first right working fluid can be increased or decreased, independently of the left fluid regulator 120A.

The apparatus 600 can sense the left eye environment over the left eye, such as with a left sensor 130A, and the right eye environment over the right eye, such as with a right sensor 130B. In an example, the left sensor 130A can sense the left eye environment independently from the right environment and the right sensor 130B can sense the right eye environment independently from the left environment.

In an example, the left sensor 130A, such as a left cavity sensor in communication with the left cavity 112A, can sense an indication of the left eye environment in the left cavity 112A. The left cavity sensor can include at least one of a left flow sensor to sense an indication of fluid flow in the left cavity 112A, a left humidity sensor to sense an indication of humidity in the left cavity 112A, a left temperature sensor to sense an indication of temperature in the left cavity 112A, a left pressure sensor to sense an indication of pressure in the left cavity 112A, or a left composition sensor to sense an indication of working fluid composition, such as working fluid constituent concentration, in the left cavity 112A.

In an example, the right sensor 130B, such as a right cavity sensor in communication with the right cavity 112B, can sense an indication of the right eye environment in the right cavity 112B. The right cavity sensor can include at least one of a right flow sensor to sense an indication of fluid flow in the right cavity 112B, a right humidity sensor to sense an indication of humidity in the right cavity 112B, a right temperature sensor to sense an indication of temperature in the right cavity 112B, a right pressure sensor to sense an indication of pressure in the right cavity 112B, or right working fluid composition, such as right working fluid constituent concentration. In an example, the left sensor 130A can sense an indication of the left eye environment in the left cavity 112A independently of the right sensor 130B, and the right sensor 130B can sense an indication of the right eye environment in the right cavity 112B independently of the left sensor 130A.

Figure 7:
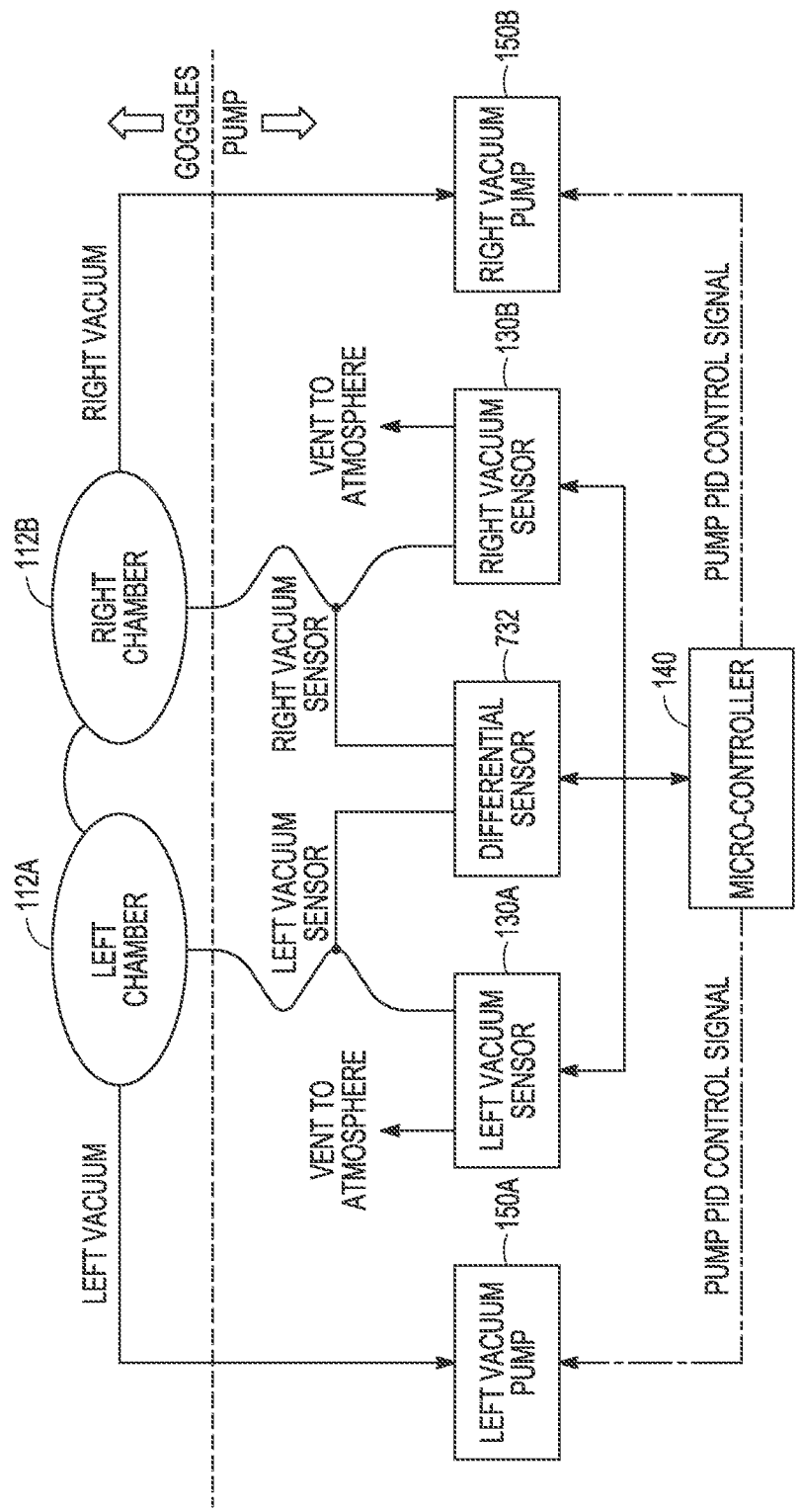
FIG. 7 shows a schematic diagram of an example apparatus that can include a sensor, such as a redundant sensor, in accordance with at least one example of the present disclosure.

With reference to FIG. 7, The apparatus 600 can process the indication of the eye environment sensed by the sensor 130, such as at least one of the left sensor 130A, the right sensor 130B, or a redundant sensor 732, with the control circuitry 140. In an example, the control circuitry 140 can include left control circuitry including a left display that can process and display at least one of an indication of the left sensor 130A or an indication of the redundant sensor 732 and right control circuitry including a right display that can process and display at least one of an indication of the right sensor 130B or an indication of the redundant sensor 732.

FIG. 7 shows a schematic diagram of an example apparatus 600 that can include a sensor 130, such as a redundant sensor 732. The redundant sensor 732 can be in communication with the cavity 112, such as in communication with at least one of the left cavity 112A, the right cavity 112B, the left sensor 130A or the right sensor 130B.

The redundant sensor 732 can be configured to sense an indication of the eye environment, such as at least one of an indication of the left eye environment in the left cavity 112A, an indication of a right eye environment in the right cavity 112B, or an indication of a relationship between the indication of the left eye environment and the indication of the right eye environment. In an example, the redundant sensor 732 can be configured to verify or otherwise confirm the proper operation of a sensor 130, such as at least one of the left sensor 130A or the right sensor 130B, monitored by the redundant sensor 732.

The redundant sensor 732 can include a differential sensor, such as a differential sensor including a left differential sensor in communication with the left cavity and a right differential sensor in communication with the right cavity, to sense at least one of an indication of the left eye environment, an indication of the right eye environment, or an indication of a relationship between the indication of the left eye environment and the indication of the right eye environment. In an example, the differential sensor can sense a difference between the indication of the left eye environment, such as an indication of pressure in the left cavity 112A, and the indication of the right eye environment, such as an indication of pressure in the right cavity 112B.

The left differential sensor can include at least one of a left differential flow sensor to sense an indication of fluid flow in the left cavity 112A, a left differential humidity sensor to sense an indication of humidity in the left cavity 112A, a left temperature sensor to sense an indication of temperature in the left cavity 112A, a left differential pressure sensor to sense an indication of pressure in the left cavity 112A, or a left differential composition sensor to sense an indication of working fluid composition, such as working fluid constituent concentration, in the left cavity 112A. The left differential sensor can include a left differential signal sensor, in communication with the sensor 130, such as at least one of the left sensor 130A or the right sensor 130B, to receive an indication of the eye environment sensed by the sensor 130, such as an electrical signal representative of the indication of the eye environment sensed by the sensor 130.

The right differential sensor can include at least one of a right differential flow sensor to sense an indication of fluid flow in the right cavity 112B, a right differential humidity sensor to sense an indication of humidity in the right cavity 112B, a right differential temperature sensor to sense an indication of temperature in the right cavity 112B, a right differential pressure sensor to sense an indication of pressure in the right cavity 112B, or right differential composition sensor to sense an indication of working fluid composition, such as working fluid constituent concentration in the right cavity 112B. The right differential sensor can include a right differential signal sensor, in communication with the sensor 130, such as at least one of the left sensor 130A or the right sensor 130B, to receive an indication of the eye environment sensed by the sensor 130, such as an electrical signal representative of the indication of the eye environment sensed by the sensor 130.

Figure 8:
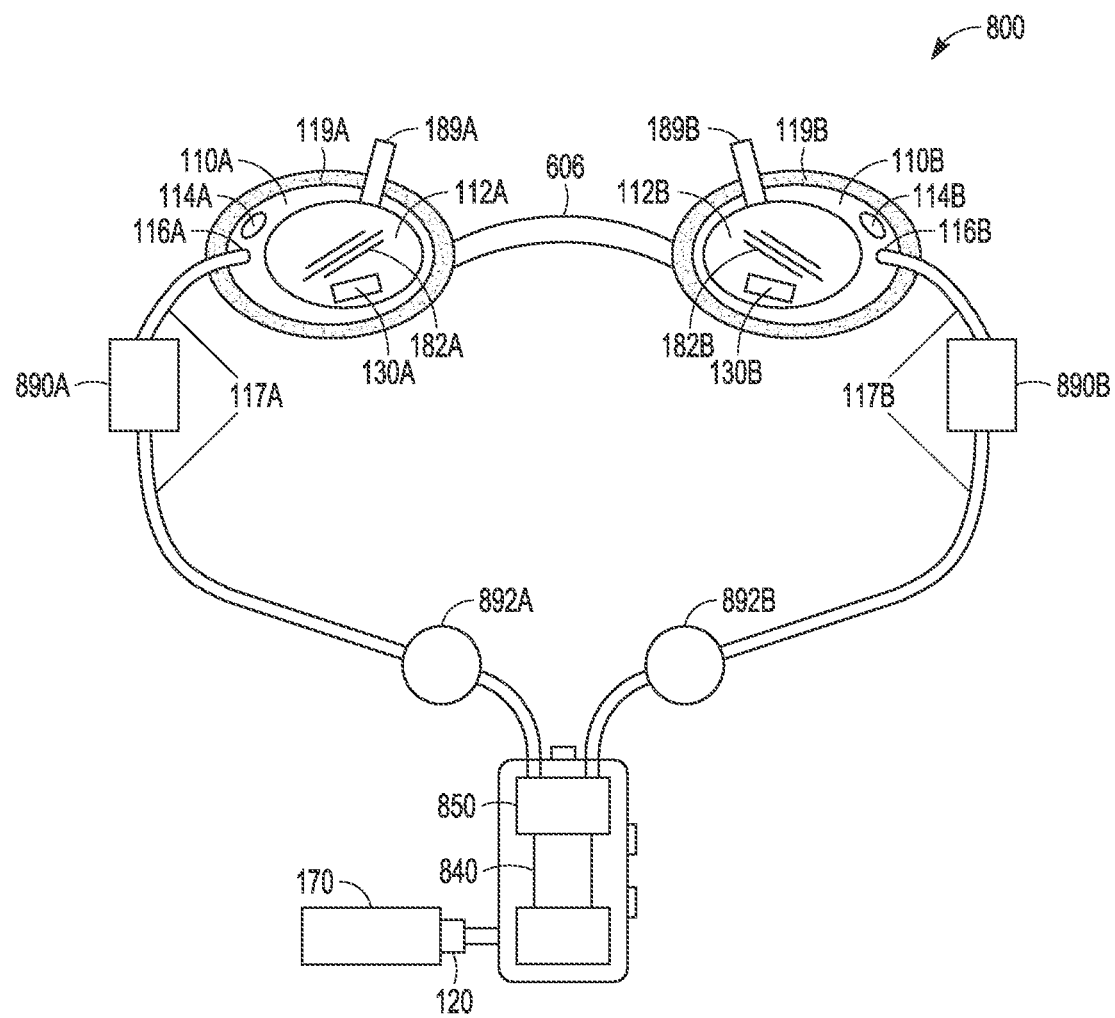
FIG. 8 shows an example of an apparatus that can independently control a left eye environment over a left eye of a patient and a right eye environment over a right eye of the patient with a single pressure source.

FIG. 8 shows an example of an apparatus 800 that can independently control a left eye environment over a left eye of a patient and a right eye environment over a right eye of the patient, such as with a single pressure source. The apparatus 800 can include at least one of a cavity valve 890 or a cavity reservoir 892.

The apparatus 800 can include a cavity valve 890, such as the cavity valve 890 in communication with the cavity 112. The cavity valve 890 can be in communication with, such as coupled to, at least one of the sensor 130, the control circuitry 140, or the pressure source 150. In an example, the cavity valve 890 can include at least one of a left control valve 890A in communication with the left cavity 112A or a right control valve 890B in communication with the right cavity 112B.

The cavity valve 890 can control working fluid pressure in the cavity 112, such as to achieve a target cavity pressure in the cavity 112. Referencing FIG. 8, the left control valve 890A can control working fluid pressure in the cavity 112A and the right control valve 890B can control working fluid pressure in the cavity 112B.

The cavity valve 890 can include a passive cavity valve, such as a passive cavity check valve 189 as described earlier in this application. The cavity valve 890 can include a single passive cavity check valve 189, such as to maintain a pressure in the cavity 112 in the absence of continuous operation of a pressure source 850. Absence of continuous operation of the pressure source 850 can include many advantages, such as to increase the battery life of a battery-powered pressure source 850.

The passive cavity check valve 189 can include a positive pressure cavity check valve. In an example, the pressure source 850 can be energized, such as to cause working fluid to flow from the pressure source 850 through the positive pressure cavity check valve to the cavity 112, to create a positive gauge pressure in the cavity 112. If the pressure source 850 is de-energized, such as if the pressure source 850 is turned off for a period of time, the positive pressure cavity check valve can close, such as to maintain the positive gauge pressure in the cavity 112. A sensor 130, such as in communication with at least one of the control circuitry 840 or the pressure source 850, can sense pressure in the cavity 112 and re-energize the pressure source 850, such as when the positive gauge pressure in the cavity 112 can drop below a threshold pressure level including a target positive cavity pressure level.

The passive cavity check valve 189 can include a negative pressure cavity check valve. In an example, the pressure source 850 can be energized, such as to draw working fluid from the cavity 112 through the negative pressure cavity check valve to the pressure source 850, to create a negative gauge pressure in the cavity 112. If the pressure source 850 is de-energized, such as if the pressure source 850 is turned off for a period of time, the negative pressure cavity check valve can close, such as to maintain the negative gauge pressure in the cavity 112. A sensor 130, such as in communication with at least one of the control circuitry 840 or the pressure source 850, can sense pressure in the cavity 112 and re-energize the pressure source 850, such as when the negative gauge pressure in the cavity 112 can rise above a threshold pressure level including a target negative cavity pressure level.

The cavity valve 890 can include a combination of one or more passive cavity check valves 189, such as a passive combination cavity valve to achieve a target cavity pressure range in the cavity 112. In an example, the cavity valve 890 can include at least one of a left passive combination cavity valve 890A or a right passive combination cavity valve 890B. The target cavity pressure range can be defined by an upper target cavity pressure level and a lower target cavity pressure level, such that the upper target cavity pressure level can be greater than the lower target cavity pressure level. In an example, the passive combination cavity valve can include a first passive cavity check valve, such as with a first cracking pressure selected as the upper target cavity pressure level, and a second passive cavity check valve, such as with a second cracking pressure selected as the lower target cavity pressure level.

The passive combination cavity valve can be used as a safety device, such as to prevent damage to the patient eye from excessive positive or negative applied pressure including excessive pressure experienced from improper or unexpected operation of the pressure source 850. In an example, positive gauge pressure can be applied to the cavity 112 in communication with the passive combination cavity valve operating as a safety device, such as with a first cracking pressure selected to be greater than a positive target cavity pressure level including 10%, 20%, 30%, 40%, or 50% greater than the positive target cavity pressure level and a second cracking pressure selected at about 0 mmHg gauge pressure. In this configuration, the apparatus 800 can protect against excessive positive pressure with the first cracking pressure and excessive negative pressure with the second cracking pressure. In an example, negative gauge pressure can be applied to the cavity 112 in communication with the passive combination cavity valve operating as a safety device, such as with a first cracking pressure selected to be less than a negative target cavity pressure level including 10%, 20%, 30%, 40%, or 50% less than the negative target cavity pressure level and a second cracking pressure selected at about 0 mmHg gauge pressure. In this configuration, the apparatus 800 can protect against excessive negative pressure with the first cracking pressure and excessive positive pressure with the second cracking pressure.

The passive combination cavity valve can be used as a metering device, such as to vary pressure in the cavity 112 based on working fluid flow from the pressure source 850 and orifice area of the cavity valve 890. In an example, the passive combination cavity valve can be specified to create pressure in the cavity 112, such as based on a volume-pressure characteristic of the pressure source 850 including a p-Q curve.

The cavity valve 890 can include an active cavity valve. In an example, the cavity valve 890 can include at least one of a left control valve 890A or a right control valve 890B. An active cavity valve can include a flow metering portion, such as a valve component to control flow through the active cavity valve, and an actuation portion, such as an actuator component to adjust the flow metering portion. In an example, an active cavity valve can include at least one of a servo valve or a proportional valve, such as a servo or proportional valve configured for use with at least one of a hydraulic working fluid or a pneumatic working fluid.

The active cavity valve can control the pressure in the cavity 112, such as to a target cavity pressure, by adjustment of the active cavity valve, such as to control fluid flow between the cavity 112 and the surrounding environment. In an example, the active cavity valve can be adjusted to allow at least one of fluid flow from the cavity 112 to the surrounding environment where the cavity pressure is greater than the surrounding environment or fluid flow from the surrounding environment into the cavity 112 where the cavity pressure is less than the surrounding environment.

The active cavity valve can be configured to adjust pressure in the cavity 112, such as from a first cavity pressure level to a second cavity pressure level different from the first cavity pressure level. The active cavity valve can adjust pressure in the cavity 112 based on a sensed indication, such as a sensed indication received and processed by the control circuitry 140. In an example, the left active cavity valve can be configured to adjust an indication of left cavity pressure based on at least one of the indications received from the left biosensor, such as at least one of an indication of left IOP level, an indication of CSFP level, an indication of a relationship between left IOP and CSFP, such as an indication of left TPD, or an indication of cardiac activity, such as at least one of systemic blood pressure or heart rate. In an example, the right active cavity valve can be configured to adjust an indication of right cavity pressure based on at least one of the indications received from the right biosensor, such as at least one of an indication of right IOP level, an indication of CSFP level, an indication of a relationship between right IOP and CSFP, such as an indication of right TPD, or an indication of cardiac activity, such as at least one of systemic blood pressure or heart rate.

In an example, the control circuitry 840 can control the cavity pressure in the left cavity 112A, such as by adjusting at least one of the pressure source 850 or the left control valve 890A to achieve a target cavity pressure in the left cavity 112A. For example, the left control circuitry 140A can be configured to include a control mechanism, such as a feedback control mechanism based on an indication from receive an indication of a physiological parameter from the left sensor 130A, such as an indication of IOP level in the left eye sensed by the left biosensor, and process the received physiological parameter, such as to adjust at least one of the pressure source 850 or the left control valve 890A, to achieve a target cavity pressure level in the left cavity 112A based on the received physiological parameter, such as the received indication of left IOP level.

In an example, the control circuitry 840 can control the cavity pressure in the right cavity 112B, such as by adjusting at least one of the pressure source 850 or the right control valve 890B to achieve a target cavity pressure in the right cavity 112B. For example, the control circuitry 840 can be configured to include a control mechanism, such as a feedback control mechanism based on an indication from receive an indication of a physiological parameter from the right sensor 130B, such as an indication of IOP level in the right eye sensed by the right biosensor, and process the received physiological parameter, such as to adjust at least one of the pressure source 850 or the right control valve 890B, to achieve a target cavity pressure level in the right cavity 112B based on the received physiological parameter, such as the received indication of right IOP level.

The apparatus 800 can include a cavity check valve 189, similar to the cavity check valve 189 as previously noted in this application. In an example, the cavity check valve 189 can include at least one of a left cavity check valve 189A, such as a left passive cavity check valve, or a right cavity check valve 189B, such as a right passive cavity check valve.

The apparatus 800 can include a cavity reservoir 892, such as the cavity reservoir 892 in communication with the cavity 112. The cavity reservoir 892 can include at least one of a left cavity reservoir 892A and a right cavity reservoir 892B.

The cavity reservoir 892 can serve to adjust an indication of system elastance in the apparatus 800, such as to improve the ability of the apparatus 800 to achieve a target cavity pressure. System elastance can be characterized by at least one of the ratio of change in pressure for a given change in volume, such as $E=\Delta P/\Delta V$, or the inverse of system compliance, such as $C=1/E=\Delta V/\Delta P$. In an example, an indication of system elastance can be equivalent to an indication of component elastance and an indication of system compliance can be equivalent to an indication of component compliance. A fluidic system with "high" elastance implies a fluidic system that can experience rapid pressure change as a function of volume change. In an example, an active cavity valve can fail to achieve the target cavity pressure in an apparatus 800 with high elastance, such as due to slow feedback response resulting in overshooting the target cavity pressure. By adjusting elastance, such as by reducing system elastance or increasing system compliance, control of the apparatus 800 can be improved, such as by reducing the rate of pressure change due to volume change to minimize feedback tracking error.

The cavity reservoir 892 can include a supplementary volume, such as a volumetric space in communication with the cavity 112, including at least one of a fluidic accumulator or an expansion chamber. In an example, a supplementary volume can be defined as any additional volume of the cavity 112, such as any component in fluidic communication with the cavity 112, beyond the minimum volume required to convey pressure to the patient eye.

The amount of supplementary volume in the cavity reservoir 892 can be selected, such as to adjust the system elastance to change system lag and error when pressurizing the apparatus 800. Supplementary volume can be adjusted from a first supplementary volume level to a second supplementary volume. In an example, the second supplementary volume level can be less than the first supplementary volume level, such as to increase system elastance. In increasing system elastance, system lag for the apparatus 800, including pressure system lag, can be reduced. In an example, the second supplementary volume level can be greater than the first supplementary volume level, such as to reduce system elastance. In reducing system elastance, system lag for the apparatus 800, including pressure system lag, can be increased.

The cavity reservoir 892 can include a compliant portion of the apparatus 800, such as a compliant portion of the apparatus 800 in communication with the cavity 112. A compliant portion can include a portion of the apparatus 800 in fluidic communication with the cavity 112, such as a portion of the apparatus 800 that demonstrates a percentage variation in component compliance greater than the least compliant component of the cavity 112 or any component in fluidic communication with the cavity 112. The percentage variation in component compliance can be in a range of at least one of about 1% to about 25%, about 25% to about 50%, about 50% to about 75%, or about 75% to about 100% as compared to the least compliant component of the system.

The compliant portion can include an elastic portion, such as a portion of the apparatus 800 in communication with the cavity 112 that demonstrates a percentage variation in component compliance greater than the least compliant component of the system. In an example, an elastic portion can include a membrane, such as the flexible septum as noted previously in this application.

The apparatus 800 can include system control circuitry 840, similar to the control circuitry 140 including left control circuitry 140A and right control circuitry 140B as previously noted in this application. The control circuitry 840 can be configured to include left system control circuitry, such as left system control circuitry configured to receive an indication of the left eye environment, such as from the left sensor 130A including the left biosensor and adjust pressure in the left cavity with the left control valve 890A toward a left target IOP based on at least one of the received indication of the left eye environment, such as the received indication of left IOP. The control circuitry 140 can be configured to include right system control circuitry, such as right system control circuitry configured to receive an indication of the right eye environment, such as from the right sensor 130A including the right biosensor and adjust pressure in the right cavity with the right control valve 890B toward a right target IOP based on at least one of the received indication of the right eye environment, such as the received indication of right IOP.

The left control circuitry can be configured to adjust left pressure in the left cavity 112A with the left active valve to equalize an indication of left translaminar pressure difference (TPD) associated with the left eye. The right control circuitry can be configured to adjust right pressure in the right cavity with the right active valve to equalize an indication of right translaminar pressure difference (TPD) associated with the right eye. In an example equalizing the indication of TPD can include reducing the indication of TPD from a first TPD level to a lower second TPD level, such as from at least one of a first left TPD level to a lower second left TPD level or a first right TPD level to a lower second right TPD level.

The left control circuitry can be configured to adjust left pressure in the left cavity with the left active valve sufficient to enhance an indication of axonal transport in the left optic nerve of the left eye and the right control circuitry can be configured to adjust right pressure in the right cavity with the right active valve sufficient to enhance an indication of axonal transport in the right optic nerve of the right eye. In an example, enhancing an indication of axonal transport can include adjusting the rate of axonal transport, such as increasing the rate of axonal transport, from a first axonal transport level to a second axonal transport level, such as where the second axonal transport level can be greater than the first axonal transport level. In an example, enhancing an indication of axonal transport can include adjusting the rate of axonal transport, such as decreasing the rate of axonal transport, from a first axonal transport level to a second axonal transport level, such as where the second axonal transport level can be less than the first axonal transport level.

The apparatus 800 can include a pressure source 850, similar to the pressure source 150 as previously noted in this application. The pressure source 850 can be configured to apply non-ambient pressure to the apparatus 800, such as at least one of the left cavity 112A or the right cavity 112B. In an example, the pressure source 850 can be configured to pressurize or otherwise apply non-ambient pressure to both the left cavity 112A and the right cavity 112B, such as to the left and right cavities 112A, 112B simultaneously.

Figure 9:
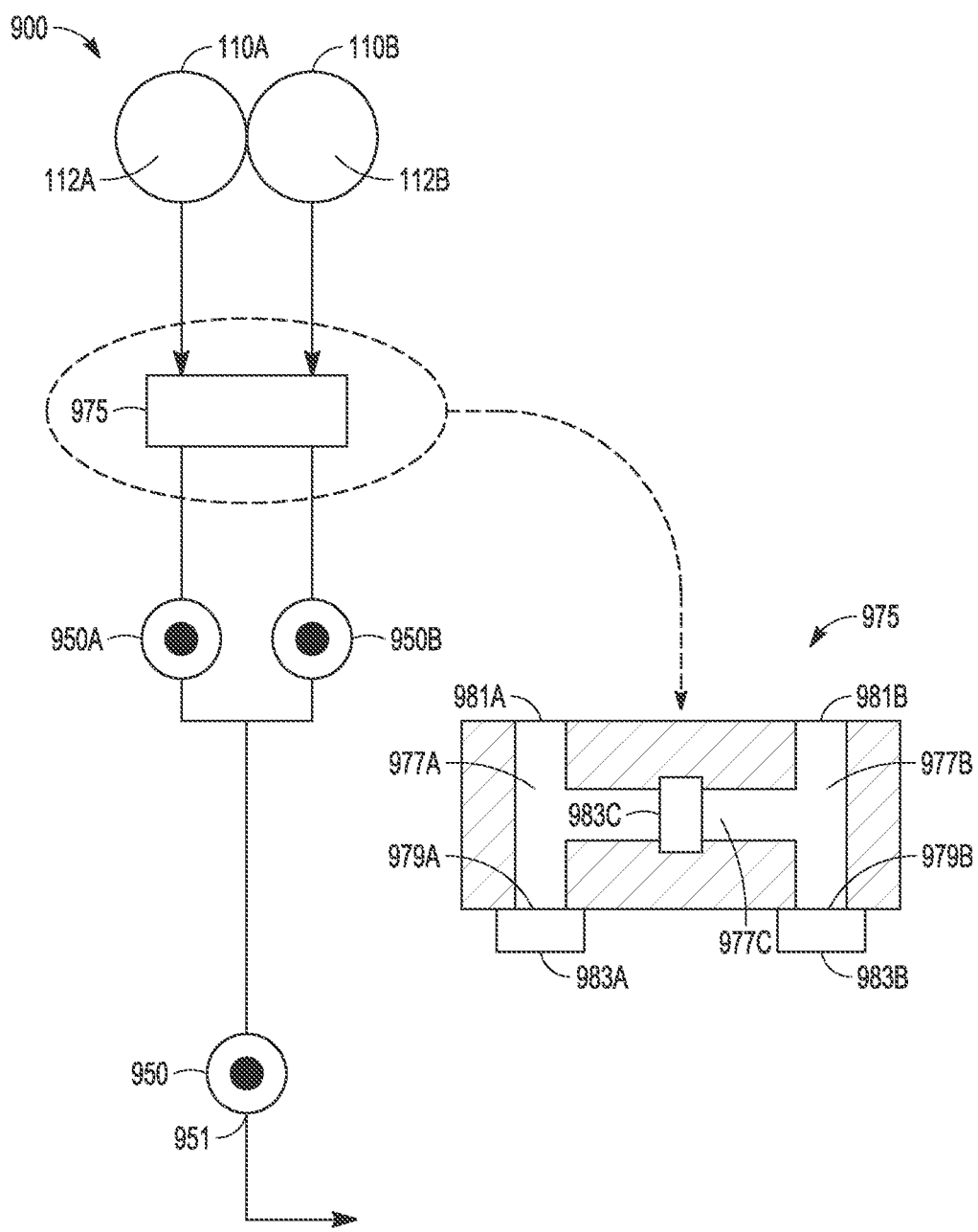
FIG. 9 shows a schematic diagram of an example apparatus that can control an eye environment over a patient eye with at least one of a main pressure source, a left pressure source, or a right pressure source.

FIG. 9 shows a schematic diagram of an example apparatus 900 that can control an eye environment over a patient eye with at least one of a main pressure source, a left pressure source, or a right pressure source, such as at least one of a left eye environment over the left patient eye or a right eye environment over the right patient eye.

The apparatus 900 can include a main pressure source 950, such as a pressure source similar to the pressure source 150, in communication with a left pressure source 950A, such as a pressure source similar to the left pressure source 150A, and a right pressure source 950B, such as a pressure source similar to the right pressure source 150A. The main pressure source 950 can draw working fluid from the surrounding environment, such as at port 951.

The apparatus 900 can include a manifold 975 to direct working fluid flow from the pressure source, such as including at least one of the main source 950, the left source 950A, or the right source 950B, to at least one of the left cavity 112A of left cover 110A or the right cavity 112B of right cover 110B. The manifold 975 can include a left column 977A with an inlet port 979A and an outlet port 981A, a right column 977B with an inlet port 979B and an outlet port 981B, and a central column 977C in communication with the left column 977A and the right column 977B. The manifold 975 can include a control valve, such as an electrically-modulated control valve including a servo valve or a proportional valve, including a left control valve 983A located in proximity to the left inlet port 979A to control left working fluid flow into the left column 977A, a right control valve 983B located in proximity to the right inlet port 979B to control right working fluid flow into the right column 977B, and a center control valve 983C in communication with the central column 977C to control the flow of left and right working fluid flows between the left and right columns 977A and 977B.

The apparatus 900 can control an indication of the eye environment over the left and right patient eye, such as control of an indication of left pressure in the left cavity 112A can be independent of an indication of right pressure in the right cavity 112B and the indication of right pressure in the right cavity 112B can be independent of the indication of left pressure in the left cavity 112B. In an example, the left and right control valves 983A, 983B can be in an open state, such as to maximize volumetric flow through the left and right control valves 983A, 983B and the center control valve 983C can be in a closed state, such as to prevent volumetric flow through the center control valve 983C to isolate the left cavity 112A from the right cavity 112B and similarly, the right cavity 112B from the left cavity 112A. The main pressure source 950 can be energized to generate a main volumetric fluid flow in the apparatus 900, such as to create an approximately equal main volumetric flow in the left and right columns 977A, 977B. The main pressure source 950 can be operated such as to generate at least one of a positive gauge pressure or a negative gauge pressure in the left and right cavities 112A, 112B.

Each of the left and right covers 110A, 110B can include a seal 119A, 119B, such as to control fluid flow into and out of the cavities 112A, 12B. In an example, the seal 119A, 119B can control ingress of ambient air into the left and right cavities 112A, 112B, such as when the left and right cavities 112A, 112B experience a negative gauge pressure. In an example, the seal 119A, 119B can control egress of working fluid into the surrounding environment, such as when the left and right cavities 112A, 112B experience a positive gauge pressure. Seal permeability can be controlled, such as in a range of about 0% permeability (e.g., a hermetic seal) to a range of about 100% permeability. In an example, seal permeability can be controlled to a range, such as at least one of a range of about 0% permeability to about 25% permeability, a range of about 25% permeability to about 50% permeability, a range of about 50% permeability to about 75% permeability, or a range of about 75% permeability to about 100% permeability.

Seal permeability can be affected by adjusting the cover-patient interface, such as the characteristics of the seal surface that contact the patient. A smooth seal surface, such as a sealing surface in complete contact with the patient, can form a continuous sealing surface around the periphery of the patient eye, such as to create a hermetic seal between the cover 110A, 110B and the patient. A non-smooth surface, such as a sealing surface in less than complete contact with the patient, can form a semi-continuous sealing surface around the periphery of the patient eye, such as to create a semi-permeable seal between the cover 110A, 110B and the patient. A non-smooth surface can include a surface formed by a material with a non-smooth surface finish including synthetic leather and an elastomer including an elastomer with a formed surface feature, such as at least one or more of a molded protuberance or a molded indentation formed in a surface of the elastomer that prevents the formation of a continuous sealing surface around the periphery of the patient eye.

Seal permeability can be affected by a characteristic of the seal material, such as at least one of the porosity of the seal material, the size of the pore in the seal material, or the distribution of pore size in the seal material. In an example, the seal material can be formed with a specified total porosity, such as in a range from about 0% porosity to about 100% porosity.

The eye environment in the cavity 112A, 112B can be affected by a feature of the cover 110A, 110B, such as the cover feature can affect a change in the eye environment similar to the effect of seal permeability. In an example, the cover feature can include a vent port, such as one or more vent ports, that can extend from an outer surface 187 of the cover 110 to an inner surface 188 of the cover 110 to place the cavity 112 in communication with the surrounding environment.

Adjustment of the eye environment can be affected by a characteristic of the vent port, such as at least one of the vent port surface area including the total vent port surface area or the number of vent ports in the cover 110A, 110B. Vent port surface area can affect the rate of fluid exchange between the cavity 112 and the surrounding environment, such as the rate of fluid exchange can depend on the surface area of the vent port. The number of vent ports can affect the rate of fluid exchange, such as the number of vent ports can affect the total vent port surface area where the rate of fluid exchange between the cavity 112 and the surrounding environment can depend on the total surface area of the vent port.

Pressure in the left and right cavities 112A, 112B can be varied such as by adjusting the resistance presented to the main volumetric fluid flow in the apparatus 900. In an example, the open state of at least one of the left or right control valve 983A, 983B can be adjusted, such as in a range between about 0% open and 100% open, to present a resistance to the main volumetric fluid flow and thereby adjusting the main volumetric fluid flow in the left and right columns 977A, 977B. As a result, gauge pressure in the left and right cavities 112A, 112B can be varied as a function of the aperture area presented by the left and right control valves 983A, 983B.

Pressure in the left and right cavities 112A, 112B can be varied such as by changing the total volumetric fluid flow in the apparatus 900. In an example, the left source 950A and the right source 950B can be energized to generate a left volumetric fluid flow due to the left source 950A and a right volumetric fluid flow due to the right source 950B. The left and right sources 950A, 950B can be energized independently, such as the left volumetric flow due to the left source 950A can be different from the right volumetric flow due to the right source 950B. In modulating the amount of energy applied to each of the left and right sources 950A, 950B, independent left and right volumetric flows can allow for independent control of the indication of left pressure in the left cavity 112A and the indication of right pressure in the right cavity 112B.

Figure 10:
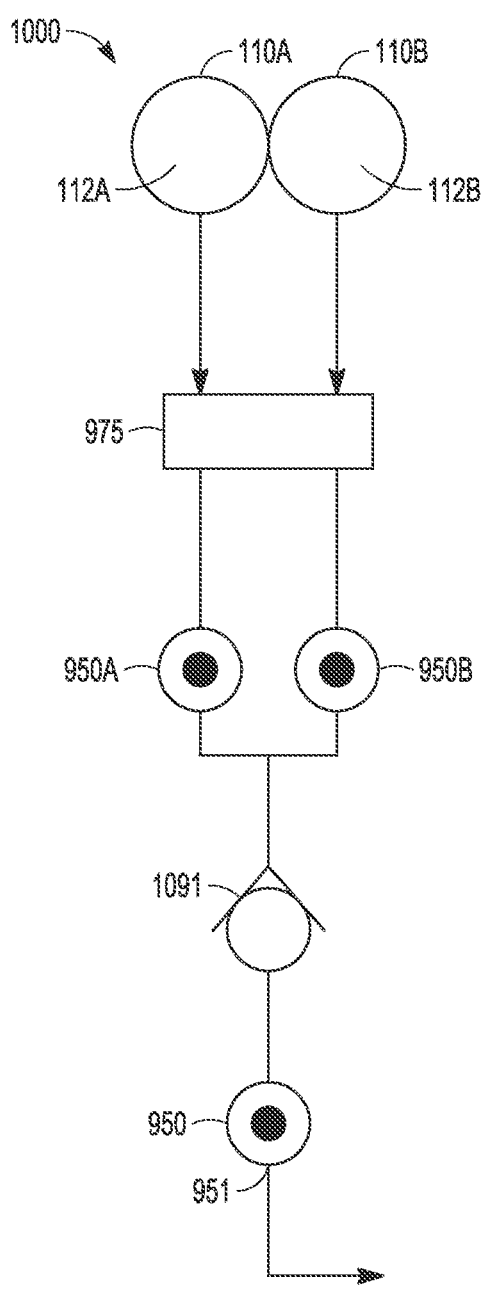
FIG. 10 shows a schematic diagram of a second example apparatus that can control an eye environment over a patient eye with a one-way valve in communication with a main pressure source.

Similarly, the apparatus 900 can control an indication of the eye environment over the left and right patient eye, such as control of the indication of left pressure in the left cavity 112A can be dependent on the indication of right pressure in the right cavity 112B and the indication of right pressure in the right cavity 112B can be dependent on the indication of left pressure in the left cavity. In an example, the center control valve 983C can be open, such as in a range between about 0% open and 100% open, to place the left cavity 112A in communication with the right cavity 112B and the right cavity 112B in communication with the left cavity 112A. In modulating the amount of energy applied to each of the left and right sources 950A, 950B, independent left and right volumetric flows can intermingle through the center control valve 983C, such as the left pressure in the left cavity 112A can depend on the right source 950B and the right pressure in the right cavity 112B can depend on the left source 950A. In an example, the left and right control valves 983A, 983B can be open, such as in a range between about 0% open and 100% open, to throttle at least one of the left volumetric flow due to the left source 950A or the right volumetric flow due to the right source 950B, such as the left pressure in the left cavity 112A can depend on the right source 950B and the right pressure in the right cavity 112B can depend on the left source 950A FIG. 10 shows a schematic diagram of a second example apparatus 1000 that can control an eye environment over a patient eye with a one-way valve in communication with a main pressure source 950, such as at least one of a left eye environment over the left patient eye or a right eye environment over the right patient eye. The apparatus 1000 can be similar to the apparatus 900 and can include a one-way valve 1091, such as a valve that can allow fluid flow in a forward direction but prevents fluid flow in a reverse direction. The one-way valve 1091 can be located in communication with the main pressure source 950, the left pressure source 950A and the right pressure source 950B, such as between the main pressure source 950 and the left and right pressure sources 950A, 950B.

The one-way valve 1091 can be oriented with the forward direction toward the left and right cavities 112A, 112B. On energizing the main pressure source 950 (e.g., turning the pressure source 950 "on"), the one-way valve 1091 can open due to flow from the main pressure source 950 into the left and right cavities 112A, 112B, such as to generate positive gauge pressure in the cavities 112A, 112B. On de-energizing the main pressure source 950 (e.g., turning the pressure source 950 "off"), the one-way valve 1091 can close, such as to maintain positive gauge pressure in the left and right cavities 112A, 112B. Gauge pressure in the left and right cavities 112A, 112B can be modulated, such as adjusted to increase or decrease gauge pressure, by energizing the left and right pressure sources 950A, 950B, such as to generate volumetric flow into the apparatus 900 (e.g., cavity gauge pressure can increase) or to generate volumetric flow from the apparatus 900 (e.g., cavity gauge pressure can decrease).

In an example, left and right positive gauge pressure in the left and right cavities 112A, 112B can be independently adjusted, such as by creating a positive gauge pressure with the main pressure source 950 and closing the control valves 983A, 983B, and 983C, such as to maintain and isolate the positive gauge pressure in the left and right cavities 112A, 112B. Left and right pressure sources 950A, 950B can be independently energized to modulate gauge pressure in the left and right cavities 112A, 112B, such as to increase or decrease positive gauge pressure in left cavity 112A independently of the right cavity 112B.

The one-way valve 1091 can be oriented with the forward direction toward the main pressure source 950. On energizing the main pressure source 950 (e.g., turning the pressure source 950 "on"), the one-way valve 1091 can open due to flow from the left and right cavities 112A, 112B to the main pressure source 950, such as to generate negative gauge pressure in the cavities 112A, 112B. On de-energizing the main pressure source 950 (e.g., turning the pressure source 950 "off"), the one-way valve 1091 can close, such as to maintain negative gauge pressure in the left and right cavities 112A, 112B.

In an example, the left and right pressure in the left and right cavities 112A, 112B, can be independently adjusted, such as by creating a negative gauge pressure with the main pressure source 950 and closing the control valves 983A, 983B, and 983C, such as to maintain and isolate the negative gauge pressure in the left and right cavities 112A, 112B. Left and right pressure sources 950A, 950B can be independently energized to modulate gauge pressure in the left and right cavities 112A, 112B, such as to increase or decrease negative gauge pressure in left cavity 112A independently of the right cavity 112B.

Figure 11:
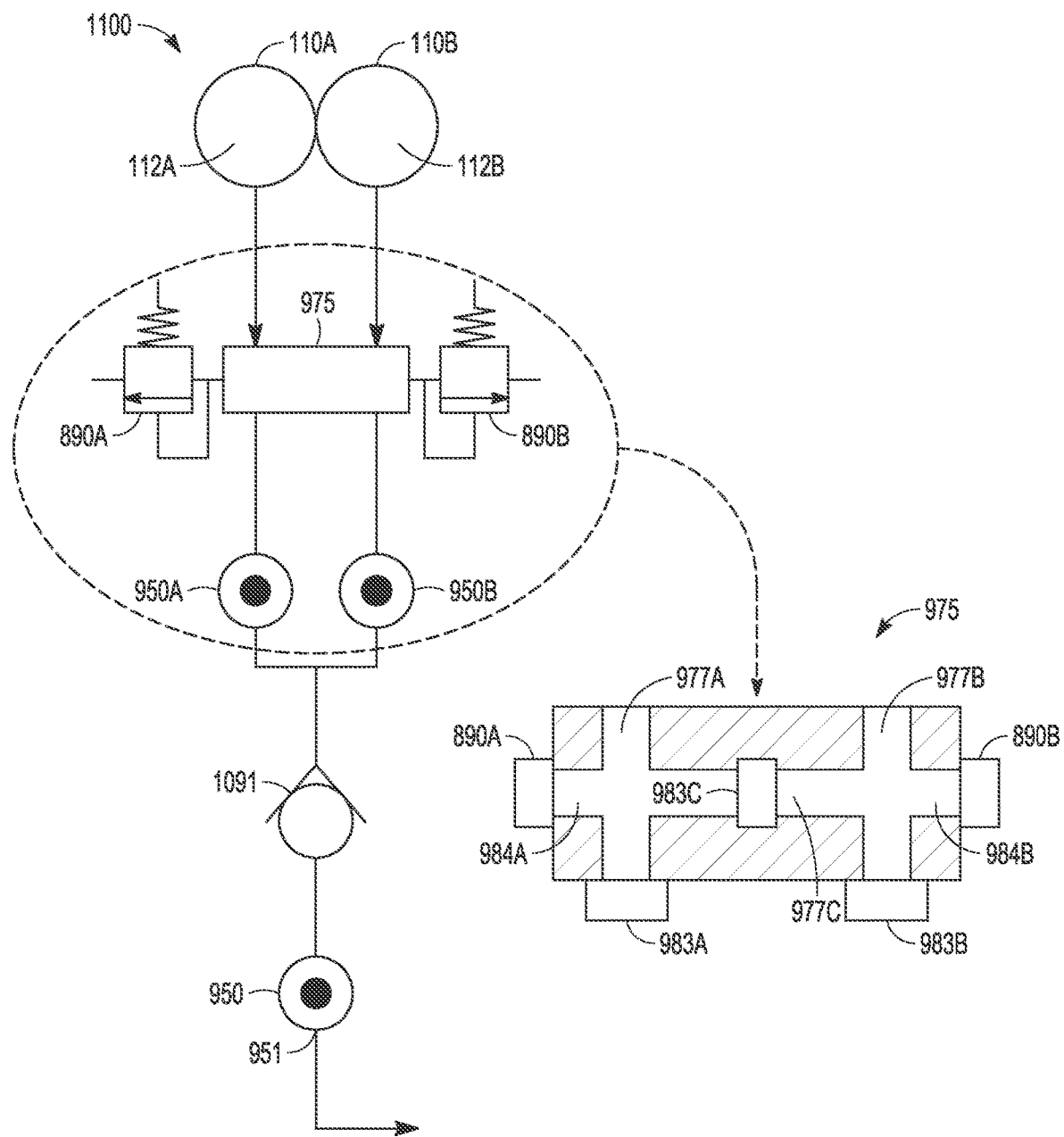
FIG. 11 shows a schematic diagram of a third example apparatus that can control an eye environment over a patient eye with a one-way valve in communication with a main pressure source and at least one of a left cavity valve or a right cavity valve.

FIG. 11 shows a schematic diagram of a third example apparatus 1100 that can control an eye environment over a patient eye with a one-way valve 1091 in communication with a main pressure source and at least one of a left control valve 890A or a right control valve 890B, such as at least one of a left eye environment over the left patient eye or a right eye environment over the right patient eye. The apparatus 1100 can be similar to the apparatus 1000 and can include a cavity valve 890 including a left control valve 890A and a right control valve 890B, such as the cavity valve 890 previously described in this application.

The left control valve 890A can be in communication with the left cavity 112A, such as attached to the manifold 975 at left side port 984A. In an example, a left side port 984A can be in communication with column 977A, such as to place the left side port 984A in communication with the left cavity 112A. The right control valve 890B can be in communication with the right cavity 112A, such as attached to the manifold 975 at right side port 984B. In an example, a right side port 984B can be in communication with column 977B, such as to place the right side port 984B in communication with the right cavity 112B.

The apparatus, such as at least one of the apparatus 100, 600, 800, 900, 1000, or 1100, can be used to treat, inhibit, or prevent an eye condition in a patient. A process, such as a diagnostic or treatment regimen, can be performed on a patient, such as the patient concerned about an eye condition or the potential existence of an eye condition. In an example, a patient can be received by a medical professional, such the patient can initiate contact with a medical professional to engage in at least one of the screening, diagnosis, or treatment of an eye condition. In an example, the patient can be selected by a medical professional, such as the patient can be contacted or otherwise invited by the medical professional to engage in at least one of the screening, diagnosis, or treatment of an eye condition. Selection by a medical professional can include selection based upon a screening criterion, such as a criterion to identify an "at-risk" patient from a population for examination by the medical professional. A screening criterion can include a patient screening criterion (or criterion particular to an individual patient), such as a physiological parameter of the patient including age, body weight, stress level, or a genetic marker. A screening criterion can include an environmental screening criterion (or criterion particular to a patient's living environment), such as residence location of the patient, patient vocation, or potential exposure to a substance identified with an eye condition.

The eye condition can manifest as a symptom, such as a symptom of the patient experiencing the eye condition. A symptom can include patient discomfort, such as pain or other vision complaint including blurry vision, or a physiological state of the patient eye, such as an abnormal indication including abnormal indications of IOP, CSFP, or cup-to-disc ratio.

Figure 12:
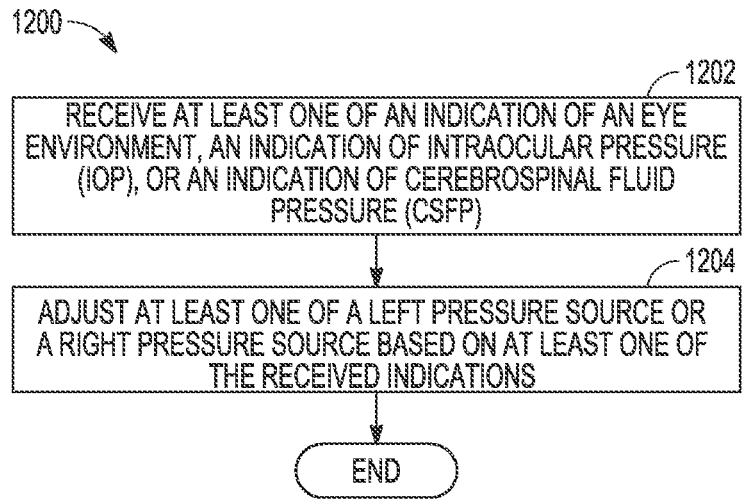
FIG. 12 shows an example method for using an apparatus to receive an indication and adjust a pressure source based on the received indication.

FIG. 12 shows an example method 1200 for using an apparatus, such as the apparatus 100, to receive an indication and adjust a pressure source based on the received indication. The apparatus 100 can include a left cover, sized and shaped to fit over a left eye of a patient to define a left cavity 112A between the left cover 110A and an anterior surface of the left eye, a left pressure source 150A, in communication with the left cavity 112A, configured to adjust fluid pressure in the left cavity 112A, a right cover 110B, sized and shaped to fit over a right eye of the patient to define a right cavity 112B between the right cover 110B and an anterior surface of the right eye, and a right pressure source 150B, in communication with the right cavity 112B, configured to adjust fluid pressure in the right cavity 112B, wherein the left pressure source 150A can be configured to adjust fluid pressure in the left cavity 112A independently of the right pressure source 150B and the right pressure source 150B can be configured to adjust fluid pressure in the right cavity 112B independently of the left pressure source 150A.

At 1202, the apparatus 100, such as at least one of the left pressure source 150A or the right pressure source 150B, can receive an indication of an eye environment, such as a left eye environment in the left cavity 112A sensed with a left sensor 130A or a right eye environment in the right cavity 112B sensed with a right sensor 130B, an indication of intraocular pressure (IOP), such as a left IOP in the left patient eye sensed by a left sensor 130A or a right IOP in the right patient eye sensed by a right sensor 130B, or an indication of cerebrospinal fluid pressure (CSFP) in the patient sensed by a left sensor 130A or a right sensor 130B. In an example, the left pressure source 150A can include left control circuitry 140A, such as to receive the sensed left indications, and the right pressure source 150B can include right control circuitry 140B, such as to receive the sensed right indications.

At 1204, at least one of the left pressure source 150A or the right pressure source 150B can be adjusted, such as based on at least one of the received indications. In an example, the left pressure source 150A can be adjusted to generate a left non-ambient pressure in the left cavity 112A based on at least one of the received left indications and the right pressure source 150B can be adjusted to generate a right non-ambient pressure in the right cavity 112B based on at least one of the received right indications.

In an example, the left pressure source 150A can receive the indication of the left eye environment, such as an indication of left pressure in the left cavity 112A, and the left pressure source 150A can be adjusted, such as based on the received indication of the left pressure in the left cavity 112A. The right pressure source 150B can receive the indication of the right eye environment, such as an indication of right pressure in the right cavity 112A, and the right pressure source 150B can be adjusted, such as based on the received indication of the right pressure in the right cavity 112B.

In an example, the left pressure source 150A can receive the indication of the left IOP from the patient left eye with the sensor 130A, such as the left IOP sensor, and the left pressure source 150A can be adjusted, such as based on the received indication of left IOP in the left patient eye. The right pressure source 150B can receive the indication of right IOP from the patient right eye with the sensor 130B, such as the right IOP sensor, and the right pressure source 150B can be adjusted, such as based on the received indication of right IOP in the right patient eye.

In an example, the left pressure source 150A can receive the indication of the left eye environment, such as the indication of left pressure in the left cavity 112A and the indication of left IOP from the patient left eye. Subsequently, the left pressure source 150A can be adjusted, such as based on the received indication of left pressure in the left cavity 112A and the received indication of left IOP in the left eye. The right pressure source 150B can receive the indication of the right eye environment, such as an indication of right pressure in the right cavity 112A, and the right pressure source 150B can be adjusted, such as based on the received indication of the right pressure in the right cavity 112B. The right pressure source 150B can receive the indication of the right eye environment, such as the indication of right pressure in the right cavity 112B and the indication of right IOP from the patient right eye. Subsequently, the right pressure source 150B can be adjusted, such as based on the received indication of right pressure in the right cavity 112B and the received indication of right IOP in the right eye.

In an example, the left pressure source 150A can receive an indication of left IOP and an indication of CSFP, such as with the left control circuitry 140A. The left control circuitry 140A can process the received indication, such as to form an indication of left translaminar pressure difference (TPD). Subsequently, the left pressure source 150A can be adjusted, such as to equalize the indication of left TPD based on the received indication of left TPD. The right pressure source 150B can receive an indication of right IOP and an indication of CSFP, such as with the right control circuitry 140B. The right control circuitry 140B can process the received indication, such as to form an indication of right translaminar pressure difference (TPD). Subsequently, the right pressure source 150B can be adjusted, such as to equalize the indication of right TPD based on the received indication of right TPD.

Equalizing the indication of TPD can include changing the indication of TPD, such as reducing the indication of TPD from a first TPD level to a lower second TPD level.

Figure 13:
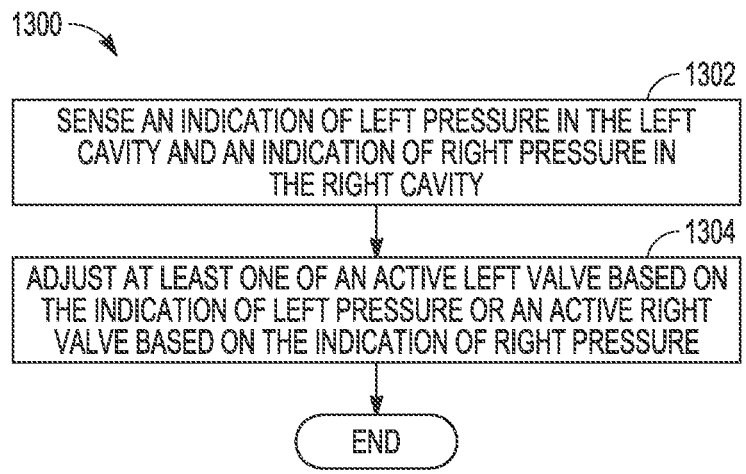
FIG. 13 shows an example method for using an apparatus to sense an indication and adjust a valve based on the sensed indication.

FIG. 13 shows an example method 1300 for using an apparatus to sense an indication and adjust a valve based on the sensed indication. The apparatus can include at least one of the apparatus 100, the apparatus 600, or the apparatus 800, or combinations of components of the aforementioned apparatus. The apparatus can include a system sensor including a left sensor 130A including a left pressure sensor in communication with a left cavity 112A to sense an indication of left pressure in the left cavity 112A, a right sensor 130B including a right pressure sensor in communication with a right cavity 112B to sense an indication of right pressure in the right cavity 112B, and a redundant sensor; system control circuitry 640, in communication with the system sensor, configured to receive and process at least one of the indication of left pressure or the indication of right pressure; an left control valve 890A in communication with the left cavity 112A and the system control circuitry 640; and an right control valve 890B in communication with the right cavity 112B and the system control circuitry 640.

At 1302, the apparatus can sense an indication pressure, such an indication of left pressure and an indication of right pressure. The left cavity 112A and right cavity 112B can be pressurized, such as to positive or negative non-ambient pressure level, with the pressure source 850. The apparatus can sense an indication of eye environment, such as an indication of pressure with the system sensor. In an example, the apparatus can sense an indication of left pressure in the left cavity 112A with the left pressure sensor, and an indication of right pressure in the right cavity 112B with the right pressure sensor.

At 1304, the apparatus can adjust a valve based on the indication of sensed pressure, such as the sensed indication of left pressure and the sensed indication of right pressure. A left valve, such as a left control valve 890A in communication with the left cavity 112A, can be adjusted, such as based on the sensed indication of left pressure in the left cavity 112A. In adjusting the left control valve 890A, pressure in the left cavity 112A can be changed, such as to achieve a target cavity pressure in the left cavity 112A. A right valve, such as a right control valve 890B in communication with the right cavity 112B, can be adjusted, such as based on the sensed indication of right pressure in the right cavity 112B. In adjusting the right control valve 890B, pressure in the right cavity 112A can be changed, such as to achieve a target cavity pressure in the right cavity 112B.

In an example, the left sensor 130A can include a left biosensor, in communication with the system control circuitry 640, configured to sense at least one of an indication of left intraocular pressure (IPO) in the left eye or an indication of cerebrospinal fluid pressure (CSFP) in the patient. The left valve, such as the left control valve 890A in communication with the left cavity 112A, can be adjusted, such as based on at least one of the sensed indication of left pressure in the left cavity 112A, the sensed indication of left IOP, or the sensed indication of CSFP. In adjusting the left control valve 890A, pressure in the left cavity 112A can be adjusted to change left pressure toward a left target IOP level, such as left pressure in the left cavity 112A can be adjusted to achieve a left IOP level including a left target IOP level in the left eye, based on the received indication of left IOP.

In an example, the right sensor 130B can include a right biosensor, in communication with the system control circuitry 640, configured to sense at least one of an indication of right intraocular pressure (IPO) in the right eye or an indication of cerebrospinal fluid pressure (CSFP) in the patient. The right valve, such as the right control valve 890B in communication with the right cavity 112B, can be adjusted, such as based on at least one of the sensed indication of right pressure in the left cavity 112A, the sensed indication of right IOP, or the sensed indication of CSFP. In adjusting the right control valve 890B, pressure in the right cavity 112B can be adjusted to change right pressure toward a right target IOP level, such as right pressure in the right cavity 112B can be adjusted to achieve a right IOP level including a right target IOP level in the right eye, based on the received indication of right IOP.

In an example, adjusting the active left valve can include adjusting the active left valve to change the left pressure in the left cavity 112A, such as to equalize an indication of left translaminar pressure difference (TPD) associated with the left eye. Adjusting the active right valve can include adjusting the active right valve to change the right pressure in the right cavity 112B, such as to equalize an indication of right translaminar pressure difference (TPD) associated with the right eye. Equalizing the indication of TPD can include changing the indication of TPD, such as reducing the indication of TPD from a first TPD level to a lower second TPD level.

In an example, adjusting the active left valve can include adjusting the active left valve to change the left pressure in the left cavity 112A, such as to achieve a left pressure sufficient to enhance an indication of axonal transport in the left optic nerve of the left eye. Adjusting the active right valve can include adjusting the active right valve to change the right pressure in the right cavity 112B, such as to achieve a right pressure sufficient to enhance an indication of axonal transport in the right optic nerve of the right eye.

Figure 14:
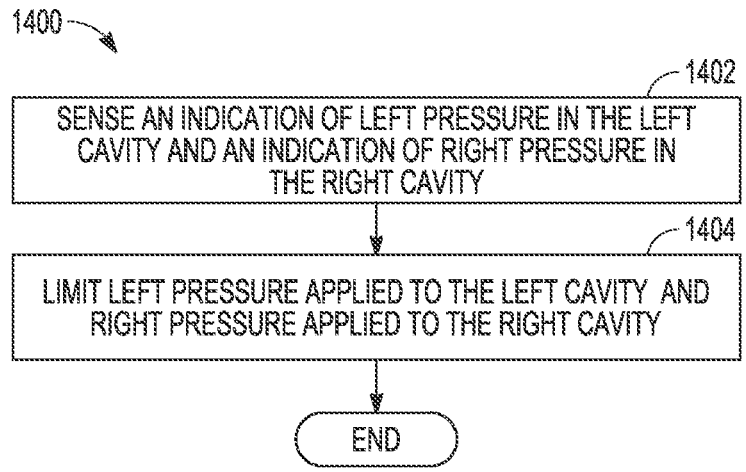
FIG. 14 shows an example method for using an apparatus to sense an indication and limit pressure applied to the cavity.

FIG. 14 shows an example method 1400 for using an apparatus to sense an indication and limit pressure applied to the cavity. The apparatus can include at least one of the apparatus 100, the apparatus 600, the apparatus 800, or combinations of components of the aforementioned apparatus. The apparatus can include a pressure source 150 in communication with a left cavity 112A located over a patient left eye and a right cavity 112B located over a patient right eye and a system sensor including a left cavity sensor 130A to sense an indication of a left eye environment in the left cavity, a right cavity sensor 130B to sense an indication of a right eye environment in the right cavity, and a redundant sensor 732 to sense a relationship between the indication of the left eye environment and the indication of the right eye environment.

At 1402, the apparatus can sense an indication pressure, such an indication of left pressure and an indication of right pressure. The left cavity 112A and right cavity 112B can be pressurized, such as to positive or negative non-ambient pressure level, with the pressure source 850. The apparatus can sense an indication of eye environment, such as an indication of pressure with the system sensor. In an example, the apparatus can sense an indication of left pressure in the left cavity 112A with the left pressure sensor, and an indication of right pressure in the right cavity 112B with the right pressure sensor.

At 1404, the apparatus can limit the pressure applied, such as to the left cavity 112A and the right cavity 112B. A valve 890, such as passive valve, can be selected, such as based on a characteristic of the valve 890 including a cracking pressure of the valve, to limit working fluid pressure in the cavity 112. Limiting pressure applied to the left cavity 112A can include at least one of selecting a left control valve 890A, such as a passive left valve in communication with the left cavity 112A, or selecting a left cracking pressure associated with the left passive valve, such as to limit left pressure applied to the left eye in the left cavity 112A. The left cracking pressure can be selected to include a left target pressure, such as a left target cavity pressure level. Limiting pressure applied to the right cavity 112B can include at least one of selecting a right control valve 890B, such as a passive right valve in communication with the right cavity 112B, or selecting a right cracking pressure associated with the right passive valve, such as limit right pressure applied to the right eye in the right cavity 112B. The right cracking pressure can be selected to include a right target pressure, such as a right target cavity pressure level.

A valve 890, such as an active valve in communication with the cavity 112, can be selected, such as to limit working fluid pressure in the cavity 112. Limiting pressure applied to the left cavity 112A can include opening an active left valve, such as based on an indication of left pressure in the left cavity 112A sensed by a left sensor 130A including a left pressure sensor. An indication of left pressure in the left cavity 112A can include an indication of the difference between an indication of left pressure in the left cavity 112A and a left safety pressure level, such as at least one of a maximum or minimum pressure level in the left cavity 112A. Limiting pressure applied to the right cavity 112B can include opening an active right valve, such as based on an indication of right pressure in the right cavity 112B sensed by a right sensor 130B including a right pressure sensor. An indication of right pressure in the right cavity 112B can include an indication of the difference between an indication of right pressure in the right cavity 112B and a right safety pressure level, such as at least one of a maximum or minimum pressure level in the right cavity 112A.

The pressure source 150 can be modulated, such as to limit working fluid pressure in the cavity 112. Modulating operation of the pressure source 150 can include adjusting pressure in the cavity 112, such as by adjusting an indication of working fluid flow rate created by the pressure source 150. The indication of working fluid flow rate can include changing operation of the pressure source 150, such as increasing or decreasing the speed of a pump to affect working fluid flow rate of the pump. Limiting pressure applied to the left cavity 112A can include modulating operation of the left pressure source 150A, such as based on at least one of left pressure in the left cavity 112A or the difference between an indication of left pressure in the left cavity 112A and a left safety pressure level. Limiting pressure applied to the right cavity 112B can include modulating operation of the right pressure source 150B, such as based on at least one of right pressure in the right cavity 112B or the difference between an indication of right pressure in the right cavity 112B and a right safety pressure level.

Various Notes & Examples

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Figure 15:
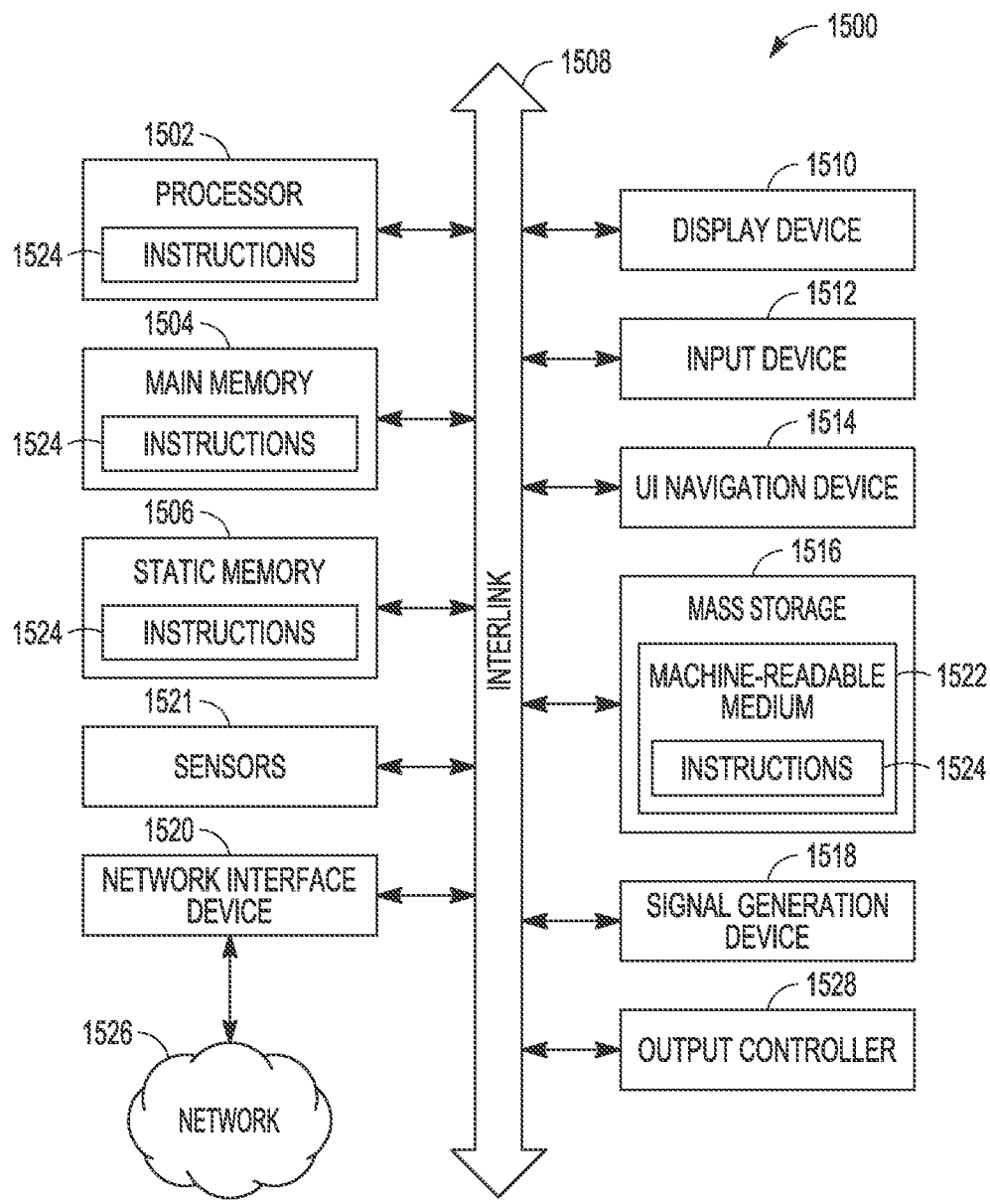
FIG. 15 shows an example block diagram of an example computing machine that can be used as control circuitry.

FIG. 15 shows an example block diagram of an example computing machine 1500 that can be used as control circuitry 140. Methods can be implemented on the control circuitry 140. The control circuitry 140 can include a computing machine 1500 upon which any one or more of the techniques or methods discussed herein can be performed. The machine 1500 may be a local or remote computer, or processing node in an on-the-go (OTG) device such as a smartphone, tablet, or wearable device. The machine 1500 may operate as a standalone device or may be connected (e.g., networked) to other machines. In an example, the machine may be directly coupled or be integrated with the apparatus 100, such as any components of the apparatus 100. It will be understood that when the processor 1502 is coupled directly to the apparatus 100, that some components of machine 1500 can be omitted to provide a lightweight and flexible device (e.g., display device, UI navigation device, etc.). In a networked deployment, the machine 1500 may operate in the capacity of a server machine, a client machine, or both in server-client network environments. In an example, the machine 1500 may act as a peer machine in peer-to-peer (P2P) (or other distributed) network environment. The machine 1500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. In an example, the machine 1500 can include a purpose-designed circuit, such as a printed circuit board that can execute the functions and methods disclosed throughout this application. Further, while only a single machine is illustrated, the term "machine" can also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuitry can include a collection of circuits implemented in tangible entities that include hardware (e.g., simple circuits, gates, logic, etc.). Circuitry membership may be flexible over time and underlying hardware variability. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, the computer readable medium is communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time.

Machine (e.g., computer system) 1500 can include a hardware processor 1502 (e.g., a central processing unit (CPU), a graphics processing unit (GPU), a hardware processor core, or any combination thereof), a main memory 1504 and a static memory 1506, some or all of which may communicate with each other via an interlink (e.g., bus) 1508. The machine 1500 may further include a display unit 1510, an alphanumeric input device 1512 (e.g., a keyboard), and a user interface (UI) navigation device 1514 (e.g., a mouse). In an example, the display unit 1510, input device 1512 and UI navigation device 1514 may be a touch screen display. The machine 1500 may additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensor. In an example, sensors 1521, such as including sensors 130, can include wearable, assistive device-based and environmental sensors, as described above. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1516 may include a machine readable medium 1522 on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media.

While the machine readable medium 1522 is illustrated as a single medium, the term "machine readable medium" may include a single medium or multiple media (e.g., a centralized or distributed database, or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communications network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system to control a left cavity fluid pressure in a left cavity formed using a left cover over an anterior surface of a patient left eye and to control a right cavity fluid pressure in a right cavity formed using a right cover over an anterior surface of a patient right eye with a pressure source couplable to at least one of the left cavity or the right cavity, the system comprising:
   control circuitry, couplable to the pressure source, the control circuitry configured to control the pressure source to independently adjust each of left cavity fluid pressure and right cavity fluid pressure,
   wherein the control circuitry includes a pressure source logic circuit configured to generate a system fault when a difference between an indication of a left eye environment and an indication of a right eye environment exceeds a safety level.

2. The system of claim 1, further comprising a differential sensor, in communication with the control circuitry, configured to sense the difference between the indication of the left eye environment and the indication of the right eye environment, wherein the differential sensor is in communication with the left cavity and the right cavity.

3. The system of claim 1, further comprising a differential pressure sensor, in communication with the control circuitry, configured to sense a difference between an indication of left cavity fluid pressure and an indication of right cavity fluid pressure, wherein the differential pressure sensor is in communication with the left cavity and the right cavity.

4. The system of claim 1, wherein the pressure source comprises a left pressure source, in communication with the left cavity and a right pressure source, in communication with the right cavity.

5. The system of claim 4, wherein at least one of the left pressure source or the right pressure source includes at least one pump to generate a target cavity fluid pressure level in at least one of the left cavity or the right cavity using a control signal from the control circuitry that is based at least in part upon an operation state of at least one of the left pressure source or the right pressure source.

6. The system of claim 1, comprising a system sensor including:
   a left cavity sensor, in communication with the left cavity, to sense an indication of a left eye environment in the left cavity;
   a right cavity sensor, in communication with the right cavity, to sense an indication of a right eye environment in the right cavity; and
   a redundant sensor configured to sense at least one of the indication of the left eye environment, the indication of the right eye environment, or an indication of a relationship between the indication of the left eye environment and the indication of the right eye environment.

7. The system of claim 1, comprising a system sensor located remote from each of the left cavity and the right cavity and in fluidic communication with at least one of the left cavity or the right cavity.

8. The system of claim 1, further comprising a multi-lumen conduit in fluid communication with at least one of the left cavity or the right cavity.

9. The system of claim 8, the conduit including a pressure apply lumen and a pressure sense lumen, wherein the conduit is configured to interrupt patency of the pressure apply lumen before interrupting patency of the pressure sense lumen during bending.

10. The system of claim 1, wherein the control circuitry is configured to process an indication of an operation state of at the pressure source to generate a target cavity fluid pressure level in at least one of the left cavity or the right cavity.

11. The system of claim 1, wherein the control circuitry is configured to generate a target cavity fluid pressure level in at least one of the left cavity or the right cavity based upon a relationship between fluid pressure and fluid flow.

12. The system of claim 1, comprising the control circuitry configured for independently establishing left cavity fluid pressure and right cavity fluid pressure based upon an indication of at least one of an intraocular pressure (IOP), a cerebrospinal fluid pressure (CSF), or a translaminar pressure difference (TPD).

13. The system of claim 1, comprising a left passive cavity check valve, in communication with the left cavity, configured to limit left cavity fluid pressure in the left cavity to a left cracking pressure and a right passive cavity check valve, in communication with the right cavity, configured to limit right cavity fluid pressure in the right cavity to a right cracking pressure.

14. The system of claim 1, comprising a left active cavity check valve, in communication with the left cavity and the control circuitry, configured to limit left cavity fluid pressure in the left cavity to a left cracking pressure and a right active cavity check valve, in communication with the right cavity, configured to limit right cavity fluid pressure in the right cavity to a right cracking pressure.

15. The system of claim 1, further comprising:
the left cover, being sized and shaped to fit over the left eye of the patient to define the left cavity between the left cover and the anterior surface of the left eye;
the right cover, being sized and shaped to fit over the right eye of the patient to define the right cavity between the right cover and the anterior surface of the right eye.

16. A method to control a left cavity eye environment in a left cavity formed using a left cover over an anterior surface of a patient left eye and to control a right cavity eye environment in a right cavity formed using a right cover over an anterior surface of a patient right eye with a pressure source couplable to at least one of the left cavity or the right cavity and control circuitry couplable to the pressure source, the control circuitry including a pressure source logic circuit configured to generate a system fault, the method comprising:
receiving an indication of a difference between an indication of a left eye environment and an indication of a right eye environment with a differential sensor in communication with the left cavity, the right cavity, and the control circuitry; and
generating a system fault with the pressure source logic circuit based on at least one of the indication of the left eye environment or the indication of the right eye environment.

17. The method of claim 16, further comprising:
receiving an indication of a setpoint level with the control circuitry; and
adjusting the pressure source toward the setpoint level.

18. The method of claim 17, wherein receiving an indication of a setpoint level includes receiving an indication of at least one of a left physiological parameter associated with the left patient eye or an indication of a right physiological parameter associated with the right patient eye; and
wherein adjusting includes adjusting toward at least one of a left target cavity pressure in the left cavity or a right target cavity pressure in the right cavity.

19. The method of claim 17, wherein receiving an indication of a setpoint level includes receiving an indication of at least one of an indication of a left intraocular pressure (IOP) in the left patient eye and an indication of a right IOP in the right patient eye; and
wherein adjusting includes adjusting toward at least one of a left target IOP cavity pressure in the left cavity or a right target IOP cavity pressure in the right cavity.

20. The method of claim 16, wherein receiving includes receiving an indication of a difference between an indication of left cavity fluid pressure and an indication of right cavity fluid pressure with the differential sensor; and
wherein generating includes generating a system fault after the indication of the difference between the indication of the left cavity fluid pressure and the indication of the right cavity fluid pressure exceeds a relationship safety pressure level.

* * * * *